(12) United States Patent
Yada et al.

(10) Patent No.: US 7,528,281 B2
(45) Date of Patent: May 5, 2009

(54) METHOD FOR VAPOR PHASE CATALYTIC OXIDATION

(75) Inventors: Shuhei Yada, Yokkaichi (JP); Hirochika Hosaka, Yokkaichi (JP); Kimikatsu Jinno, Yokkaichi (JP); Teruo Saito, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 845 days.

(21) Appl. No.: 10/864,492

(22) Filed: Jun. 10, 2004

(65) Prior Publication Data

US 2004/0250868 A1  Dec. 16, 2004

Related U.S. Application Data

(63) Continuation of application No. PCT/JP02/13372, filed on Dec. 20, 2002.

(30) Foreign Application Priority Data

| Dec. 28, 2001 | (JP) | ............................. 2001-399118 |
| Jan. 11, 2002 | (JP) | ............................. 2002-004635 |

(51) Int. Cl.
*C07C 51/16* (2006.01)
(52) U.S. Cl. ...................... 562/532; 562/545
(58) Field of Classification Search ........................ None
See application file for complete search history.

(56) References Cited

U.S. PATENT DOCUMENTS 4,072,601 A * 2/1978 Patouillet .................... 208/134

4,077,530 A  3/1978 Fukusen et al.
(Continued)

FOREIGN PATENT DOCUMENTS

BG   40018   10/1986

(Continued)

OTHER PUBLICATIONS

Zeiser et al., Chemical Engineering Science (2001), 56(4), 1697-1704.*

(Continued)

*Primary Examiner*—Karl J Puttlitz
(74) *Attorney, Agent, or Firm*—Wenderoth, Lind & Ponack, LLP.

(57) ABSTRACT

An object of the present invention is to provide a method for vapor phase catalytic oxidation which is almost free of variations in reaction states in respective reaction tubes of the fixed bed multi-tube heat-exchanger type reactor.

Provided is a method for vapor phase catalytic oxidation for obtaining a reaction product gas by using a fixed bed multi-tube heat-exchanger type reactor provided with a plurality of reaction tubes and by feeding a raw material gas inside the reaction tubes packed with a catalyst, wherein the method comprises:

adjusting pressure losses of the respective reaction tubes so that the pressure losses of the respective reaction tubes after catalyst packing is within ±20% of an average pressure loss of the reaction tubes by: packing an inert substance at a raw material gas inlet portion of the reaction tubes or removing and re-packing the catalyst packed, for a reaction tube having a pressure loss lower than the average pressure loss of the reaction tubes; and removing and re-packing the catalyst packed, for a reaction tube having a pressure loss higher than the average pressure loss of the reaction tubes.

7 Claims, 8 Drawing Sheets

U.S. PATENT DOCUMENTS

| | | | |
|---|---|---|---|
| 4,461,327 A | 7/1984 | Magin et al. | 141/1 |
| 4,571,325 A | 2/1986 | Nikolov et al. | |
| 5,177,260 A | 1/1993 | Kawajiri et al. | |
| 5,247,970 A | 9/1993 | Ryntveit et al. | |
| 5,264,627 A * | 11/1993 | Tazaki et al. | 562/599 |
| 6,333,011 B1 | 12/2001 | Schliephake et al. | |
| 6,399,818 B2 | 6/2002 | Tanimoto et al. | |
| 2001/0046463 A1 | 11/2001 | Harper et al. | |
| 2002/0136678 A1 | 9/2002 | Tanimoto et al. | |

FOREIGN PATENT DOCUMENTS

| | | |
|---|---|---|
| EP | 1 156 027 | 11/2001 |
| JP | 52-003579 | 1/1977 |
| JP | 60-112338 | 7/1985 |
| JP | 60-136344 | 9/1985 |
| JP | 05-031351 | 2/1993 |
| JP | 05-049908 | 3/1993 |
| JP | 5-97730 | 4/1993 |
| JP | 5-261272 | 10/1993 |
| JP | 6-7669 | 1/1994 |
| JP | 2001-328951 | 11/2001 |
| JP | 2002-306953 | 10/2002 |
| JP | 2003-1094 | 1/2003 |
| SU | 1 341 824 | 10/1994 |

OTHER PUBLICATIONS

Usami et al., Nippon Kikai Gakkai Ronbunshu, B-hen (2000), 66(641), 203-210.*

Borkink et al., Chemical Engineering Science (1994), 49(6), 863-76.*

Narsimhan, Industrial & Engineering Chemistry Process Design and Development (1976), 15(2), 302-7.*

Tone et al., Kagaku Kogaku (1996), 30(11), 1038-43.*

Notice of Reason for Rejection mailed Apr. 15, 2008, issued in corresponding Japanese Patent Application No. 2002-363352, and English translation thereof.

Notice of Reason for Rejection mailed Apr. 15, 2008 issued, in Japanese Patent Application No. 2002-363350, and English translation thereof.

Patent Abstracts of Japan, vol. 018, No. 061, Feb. 2, 1994 & JP 05 279269 A, Oct. 26, 1993.

Foreign reference article 547.584.002.2, pp.74-76.

Valentin Nikolov et al., "Achievements in the production of phthalic anhydride by vapour phase oxidation of o-xylene on fixed catalyst bed." Rassegne Di Scienza E Tecnologia, 72-1990, 111-114.

Valentin Nikolov et al., "Productivity of Modern Industrial Heterogeneous Catalytic Twin Processes- The Phthalic and Maleic Anhydride Syntheses." Bulgarian Chemical Communications, vol. 31, No. 3/4, pp. 505-520, 1999.

Notice of Reason for Rejection mailed May 20, 2008 in corresponding JP 2002-364643, with English translation thereof.

Notice of Reason for Rejection mailed May 20, 2008 in corresponding JP 2002-004635, with English translation thereof.

Akiyoshi Tamaki Edition, Handbook of Chemical Plant Contruction, Maruzen Kabushiki Kaisha, Oct. 25, 1972, pp. 1276-1277, with English translation thereof.

Kenji Hashimoto Edition, Industrial Reactor—Selection • Design • Working Example -, Kabushiki Kaisha Baifukan, Feb. 25, 1984, pp. 42-45, 64 and 65, with English translation thereof.

* cited by examiner

METHOD FOR VAPOR PHASE CATALYTIC OXIDATION

This application is a continuation of International Application No. PCT/JP02/13372 filed Dec. 20. 2002.

TECHNICAL FIELD

The present invention relates to a method for vapor phase catalytic oxidation involving using a fixed bed multi-tube heat-exchanger type reactor provided with a plurality of reaction tubes and feeding a raw material gas for reaction. The present invention more specifically relates to a method for vapor phase catalytic oxidation which is almost free of variations in reaction states in respective reaction tubes of the fixed bed multi-tube heat-exchanger type reactor.

In addition, the present invention relates to a method for packing a catalyst in the reaction tubes used in the method for vapor phase catalytic oxidation.

BACKGROUND ART

A fixed bed multi-tube heat-exchanger type reactor provided with a plurality of reaction tubes (hereinafter, may be referred to as "fixed bed multi-tube reactor") has been known up to now. Further, a method of vapor phase catalytic oxidation using the fixed bed multi-tube heat-exchanger type reactor has been known.

A method of packing a catalyst in the fixed bed multi-tube heat-exchanger type reactor generally involves packing by charging the catalyst from an upper portion of the reactor and allowing the catalyst to fall. However, according to this method, packed states differ for the respective reaction tubes because of reasons including: (1) the catalyst is powdered or degraded by physical impact of the catalyst charged to fall; and (2) packing time varies. To be specific, a level of powdering or degradation of the catalyst during catalyst packing differs for the respective reaction tubes. Further, long packing time results in a large packing density, and short packing time results in a small packing density. Therefore, according to a conventional packing method, the catalyst was hardly packed to provide uniform pressure states of the respective reaction tubes, particularly a pressure loss, which becomes an important factor in an oxidation reaction.

No technique exists aiming to provide a uniform pressure loss for the respective reaction tubes of the fixed bed multi-tube reactor, and methods for solving the problem (1) or (2) are proposed.

Examples of a method of suppressing powdering or degradation of the catalyst during catalyst packing include the following.

JP 2852712 B discloses a method of improving mechanical strength of a catalyst by coating the catalyst with an organic polymer compound having depolymerizing property on a surface of the catalyst. However, a uniform coating of all of the catalyst is difficult, and catalyst strength varies even if the catalyst strength increases as a whole. The coating has some effects in reducing the pressure loss, but this method is far from a satisfying method of providing a uniform pressure loss for the respective reaction tubes.

Further, JP 05-031351 A discloses a method of interposing a cord-like substance, having a shape and a thickness substantially not obstructing falling of a catalyst, inside a reactor when packing the catalyst from an upper portion of the reactor by allowing to fall. A slight effect is provided for preventing powdering or degradation of the catalyst, but an effect of catalyst packing time on packing density is unavoidable. Thus, this method is far from a satisfying method for providing a uniform pressure loss in the respective reaction tubes.

Further, JP 10-277381 A discloses a method involving packing dry ice prior to packing a catalyst by allowing to fall, packing the catalyst, and subsequently vaporizing and removing the dry ice.

Further, JP 09-141084 A discloses a method of packing a catalyst from an upper portion of a reactor involves packing a liquid substance inside the reactor, subsequently packing the catalyst, and then removing the liquid substance. However, these methods of packing the dry ice or the liquid substance in advance are far from satisfying methods industrially because post-treatment after catalyst packing involves time and effort, and handled substances may deteriorate a working environment.

On the other hand, examples of methods of controlling packing operation (time) include the following.

JP 11-333282 A discloses a method using an automatic packing machine provided with a catalyst feed conveyor and capable of controlling catalyst packing time. The patent discloses that the packing machine provides uniform packing time, allowing a uniform pressure loss in the respective reaction tubes. However, a difference in pressure loss may result depending on the catalyst, and thus, the method is far from satisfying.

Next, a fixed bed multi-tube heat-exchanger type reactor, using a heating medium for absorbing heat of reaction generated inside reaction tubes is conventionally provided with a plate for changing passage of the heating medium, called a baffle, to allow uniform flow of the heating medium inside the reactor as much as possible.

Such a fixed bed multi-tube heat-exchanger type reactor provided with a baffle did not have particular problems when a size of a plant was small. However, following problems arise when a size of the plant, that is, a reactor becomes large for increasing productivity as of today.

In other words, a non-uniform portion of a flow of the heating medium forms inside a reactor shell. A state of poor heat removal forms in part of reaction tubes among a plurality of reaction tubes inside the reactor. A localized abnormal high-temperature zone (hot spot) may form in the reaction tubes which are in a state of poor heat removal, possibly resulting in a reaction out of control.

Further, such different reaction states among the reaction tubes result in a problem of not preventing formation of reaction tubes in which a reaction becomes out of control. In addition, the different states result in problems of decreasing an yield of a target product gas and of decreasing a catalyst life.

On the other hand, an increase of raw material gas feed for enhancing the productivity results in portions where heat removal is slower than heat generation during a reaction, even with a conventional reactor of a small size. Thus, problems arise such as the above hot spots.

In other words, a conventional method for vapor phase catalytic oxidation using the fixed bed multi-tube heat-exchanger type reactor was not a method for vapor phase catalytic oxidation exhibiting satisfactory results such as effectively preventing forming of hot spots, yielding a large amount of a reaction product gas, and having a long catalyst life.

Further, the method of packing the catalyst in the reaction tubes of the fixed bed multi-tube heat-exchanger type reactor as described above generally involves using a packing funnel. The catalyst is packed by providing the reaction tubes with the packing funnel, and packing the catalyst by charging the catalyst and allowing the catalyst to fall through the packing funnel.

However, the powdered or degraded catalyst formed during transfer, transport, and handling of the catalyst is packed in the reaction tubes as well according to this method. Variations of pressure loss becomes large, which is a particularly important factor in an oxidation reaction during a production step of acrylic acid or methacrylic acid (hereinafter, may be referred to as "(meth)acrylic acid"), and thus, this method is far from a satisfying packing method for providing a uniform reaction.

Up to now, no technique is available for separating and removing the powdered or degraded catalyst in the packed catalyst during catalyst packing. The method as described above is merely proposed for suppressing powdering or degradation of the catalyst during catalyst packing.

However, those methods had problems in that powdering or degradation of the catalyst caused by vibration or impact taking place during transfer, transport, and handling of the catalyst from catalyst production to catalyst packing or the like in the reaction tubes of the fixed bed multi-tube reactor were hardly evaded. In addition, the catalyst was packed in the reaction tubes of the fixed bed multi-tube reactor together with the powdered or degraded catalyst or the like.

Further, when packing a catalyst in the reaction tubes of the fixed bed multi-tube heat-exchanger type reactor, the method as described above is employed to pack the catalyst by allowing the catalyst to fall from an upper portion of the reactor.

However, the catalyst may be powdered or degraded from physical impact during falling of the catalyst according to this method. For preventing the above, the catalyst itself must have mechanical strength above some level or the packing method must be somehow devised.

The mechanical strength of the catalyst can be improved to a certain degree by adjusting a molding pressure of the catalyst or devising operations of molding or support. However, the catalyst having enhanced mechanical strength through those techniques resulted in reducing specific surface areas of the catalyst, reducing active sites effective for a reaction, and not allowing control of pore distribution effective for reaction. Thus, problems arouse such that an yield of the target product was reduced and the catalyst was not practical.

Further, examples of the method of suppressing powdering or degradation of the catalyst during catalyst packing include the above methods disclosed in JP 2852712 B, JP 05-031351 A, JP 10-277381 A, and JP 09-141084.

However, a uniform coating of all of the catalyst is difficult for the method of enhancing the mechanical strength of the catalyst by coating the catalyst, and catalyst strength varies even if the catalyst strength increases as a whole. The coating has some effects in reducing powdering or degradation of the catalyst, but this method requires a step of coating during catalyst production and is far from a satisfying method.

The method of interposing a cord-like substance provides an effect of preventing powdering or degradation of the catalyst. However, the method requires an operation of pulling the cord-like substance upward while packing the catalyst. Effects such as extending the packing operation time or the like are unavoidable, and thus, this method is far from satisfying.

The method of packing the dry ice or the liquid substance before catalyst packing may result in post treatment taking time and effort after catalyst packing and deterioration of the working environment depending on the handled substances, and thus, is far from satisfying industrially.

DISCLOSURE OF THE INVENTION

A first invention of the present invention has been made in view of the above problems, and an object of the first invention is to provide a method for vapor phase catalytic oxidation in which a vapor phase catalytic oxidation reaction through packing a catalyst in reaction tubes of a fixed bed multi-tube heat-exchanger type reactor proceeds in the respective reaction tubes having a uniform pressure loss at an optimum temperature in all reaction tubes.

The inventors of the present invention have confirmed during a periodic repair operation, for example, that some reaction tubes result in coking in a plant producing acrolein, acrylic acid, or the like through vapor phase catalytic oxidation of propylene using the fixed bed multi-tube heat-exchanger type reactor. Moreover, the reaction tubes resulting in coking are scattered, and the coking occurs without a pattern in places where cannot be explained by a reaction gas flow or a heating medium flow inside the reactor.

The inventors of the present invention have studied intensively based on the fact, and found out that (1) a difference in pressure losses of the respective reaction tubes in the fixed bed multi-tube heat-exchanger type reactor significantly affects conditions of a reaction and (2) pressure loss of the reaction tubes after catalyst packing affects the conditions of a reaction thereafter, to thereby complete the first invention of the present invention.

Further, a second invention of the present invention has been made in view of the above problems, and an object of the second invention is to provide a method for vapor phase catalytic oxidation achieving satisfactory results such as effectively preventing hot spot formation, yielding a large amount of a reaction product gas, and extending a catalyst life. Those satisfactory results may be obtained by using a fixed bed multi-tube heat-exchanger type reactor provided with a plurality of reaction tubes, circulating a heating medium outside the reaction tubes, and feeding a raw material gas inside the reactor packed with a catalyst.

Examples of methods for preventing the formation of the hot spots include: improvements regarding equipment of the reactor such as a reduction of a reaction tube diameter, use of a heating medium having a large heat capacity, and an increase in amount of the circulating heating medium for reducing temperature of a catalyst layer inside the reaction tubes; and improvements regarding reaction conditions such as change in concentration of the raw material gas.

However, similarly and uniformly subjecting all reaction tubes in the reactor with those methods results in high cost and is not preferable also in terms of improving productivity. Further, reaction states of the respective reaction tubes inside the reactor will not be uniform according to those methods.

The inventors of the present invention have studied intensively and have confirmed that uniform reaction states of the reactions tubes inside the reactor is effective for allowing effective prevention of hot spot formation, increasing yield of a reaction product gas, and extending a catalyst life. Therefore, the inventors of the present invention have found out that the method described below provides a method for vapor phase catalytic oxidation achieving the above objects, to thereby complete the second invention of the present invention.

Further, a third invention of the present invention has been made in view of the above problems, and an object of the third invention is to provide a method of packing a catalyst or the like in reaction tubes of a fixed bed multi-tube reactor while separating and removing powdered or degraded catalyst during catalyst packing when packing a catalyst or the like in the reaction tubes of the fixed bed multi-tube reactor.

The inventors of the present invention have found out that when packing a catalyst or the like in the reaction tubes of the fixed bed multi-tube reactor, separation and removal of powdered or degraded catalyst or the like during packing catalyst is important in addition to suppression of powdering or degradation of the catalyst or the like during packing, to thereby complete the third invention of the present invention.

Further, a fourth invention of the present invention has been made in view of the above problems, and an object of the fourth invention is to provide a method of packing a catalyst in reaction tubes of a fixed bed multi-tube reactor through minimizing powdering or degradation of a catalyst having not so high mechanical strength without affecting catalyst packing operation time, when packing a catalyst in the reaction tubes of the fixed bed multi-tube reactor.

The inventors of the present invention have conducted various studies and have found out that when packing a molded catalyst or a supported catalyst by allowing the catalyst to fall from an upper portion of the reaction tubes of the fixed bed multi-tube reactor, interposing a chain substance in the reaction tubes to reduce a falling rate of the catalyst allows suppressing of blocking without affecting the catalyst packing operation time, and minimizing of powdering or degradation, to thereby complete the fourth invention of the present invention.

In other words, the first invention of the present invention is described below.

(1) A method for vapor phase catalytic oxidation for obtaining a reaction product gas by using a fixed bed multi-tube heat-exchanger type reactor provided with a plurality of reaction tubes and by feeding a raw material gas inside the reaction tubes packed with a catalyst, wherein the method comprises:

adjusting pressure losses of the respective reaction tubes so that the pressure losses of the respective reaction tubes after catalyst packing is within ±20% of an average pressure loss of the reaction tubes by: packing an inert substance at a raw material gas inlet portion of the reaction tubes or removing and re-packing the catalyst packed, for a reaction tube having a pressure loss lower than the average pressure loss of the reaction tubes; and removing and re-packing the catalyst packed, for a reaction tube having a pressure loss higher than the average pressure loss of the reaction tubes.

(2) The method for vapor phase catalytic oxidation according to the above item (1), wherein the inert substance for adjusting pressure loss is at least one type of a substance selected from the group consisting of alumina, silicon carbide, silica, zirconium oxide, and titanium oxide.

(3) The method for vapor phase catalytic oxidation according to the above item (1) or (2), wherein a shape of the inert substance for adjusting the pressure loss is spherical, cylindrical, ring-shaped, or amorphous.

(4) The method for vapor phase catalytic oxidation according to any one of the above items (1) to (3), wherein the catalyst is an Mo—Bi mixed oxide catalyst or an Mo—V mixed oxide catalyst.

(5) The method for vapor phase catalytic oxidation according to any one of the above items (1) to (4), wherein a shape of the catalyst is spherical, cylindrical, ring-shaped, or amorphous.

(6) The method for vapor phase catalytic oxidation according to any one of the above items (1) to (5), wherein the catalyst is a single catalyst or a catalyst diluted with the inert substance.

(7) The method for vapor phase catalytic oxidation according to any one of the above items (1) to (6), wherein the method further comprises:

predicting reaction states inside the reaction tubes through measurement of catalyst layer temperature of the reaction tubes or through a simulation analysis of a fluid state of a heating medium circulating outside the reaction tubes with heat of reaction inside the reaction tubes using a computer; and determining catalyst packing specifications of the reaction tubes according to the prediction results so that nonuniformity of the reaction states among the reaction tubes are reduced for packing the catalyst in the reaction tubes.

(8) The method for vapor phase catalytic oxidation according to the above item (7), wherein items determining the catalyst packing specifications include items of a catalyst type, a catalyst amount, a catalyst form, a dilution method for the catalyst, and lengths of reaction zones.

(9) The method for vapor phase catalytic oxidation according to any one of the above items (1) to (8), wherein the method further comprises:

packing the catalyst by allowing the catalyst to fall using a funnel with a net in at least a part of the funnel, for packing the catalyst in the reaction tubes.

(10) The method for vapor phase catalytic oxidation according to any one of the above items (1) to (8), wherein the method further comprises:

interposing a chain substance inside the reaction tubes so that a lower end of the chain substance is positioned above an upper end of a catalyst layer; and packing the catalyst by allowing the catalyst to fall, for packing the catalyst in the reaction tubes.

(11) A production method for (meth)acrolein or (meth)acrylic acid wherein the method comprises:

using the method for vapor phase catalytic oxidation according to any one of the above items (1) to (10); and oxidizing propane, propylene, and isobutylene using molecular oxygen to produce (meth)acrolein or (meth)acrylic acid.

In other words, the second invention of the present invention is described below.

(12) A method for vapor phase catalytic oxidation for obtaining a reaction product gas by using a fixed bed multi-tube heat-exchanger type reactor provided with a plurality of reaction tubes, circulating a heating medium outside the reaction tubes, and feeding a raw material gas inside the reaction tubes packed with a catalyst, wherein the method comprises:

predicting reaction states inside the reaction tubes; and changing catalyst packing specifications of the reaction tubes according to the prediction results so that nonuniformity of the reaction states among the reaction tubes are reduced.

(13) The method for vapor phase catalytic oxidation according to the above item (12), wherein the heating medium is for absorbing heat of reaction generated from the reaction tubes.

(14) The method for vapor phase catalytic oxidation according to the above item (12) or (13), wherein the reaction states inside the reaction tubes are predicted by grasping thermal states inside the reaction tubes.

(15) The method for vapor phase catalytic oxidation according to any one of the above items (12) to (14), wherein the thermal states inside the reaction tubes are grasped by measuring catalyst layer temperatures of the reaction tubes.

(16) The method for vapor phase catalytic oxidation according to any one of the above items (12) to (14), wherein the thermal states inside the reaction tubes are grasped through a simulation analysis using a computer.

(17) The method for vapor phase catalytic oxidation according to the above item (16), wherein a fluid analysis of a heating medium is conducted through the simulation analysis using a computer.

(18) The method for vapor phase catalytic oxidation according to the above item (17), wherein the fluid analysis of the heating medium and an analysis of heat of reaction inside the reaction tubes are conducted through the simulation analysis using a computer.

(19) The method for vapor phase catalytic oxidation according to any one of the above items (12) to (18), wherein items determining the catalyst packing specifications include items of a catalyst type, a catalyst amount, a catalyst shape, a dilution method for the catalyst, and lengths of reaction zones.

(20) The method for vapor phase catalytic oxidation according to any one of the above items (12) to (19), wherein the method further comprises:

stopping feed of the raw material gas to the reaction tubes for a part of the reaction tubes among the plurality of reaction tubes in the fixed bed multi-tube heat-exchanger type reactor.

In other words, the third invention of the present invention is described below.

(21) A method for packing a catalyst by allowing the catalyst to fall into reaction tubes of a fixed bed multi-tube reactor using a funnel, wherein at least a part of the funnel is a net.

(22) The method for packing a catalyst according to the above item (21), wherein the catalyst is a molded catalyst or a supported catalyst.

(23) The method for packing a catalyst according to the above item (21) or (22), wherein the catalyst is a catalyst for producing acrylic acid or methacrylic acid.

(24) The method for packing a catalyst according to any one of the above items (21) to (23), wherein a net mesh of the funnel is smaller than outer diameters of the catalyst and an inert substance.

(25) The method for packing a catalyst according to any one of the above items (21) to (24), wherein the net of the funnel is provided at an inclined portion of the funnel and an angle of the inclination is 10 to 75°.

In other words, the fourth invention of the present invention is described below.

(26) The method for packing a catalyst by allowing the catalyst to fall into reaction tubes of a fixed bed multi-tube reactor, wherein the method comprises:

interposing a chain substance inside the reaction tubes so that an lower end of the chain substance is positioned above an upper end of a catalyst layer; and packing the catalyst in the reaction tubes of the fixed bed multi-tube reactor.

(27) The method for packing a catalyst according to the above item (26), wherein the catalyst is a molded catalyst or a supported catalyst.

(28) The method for packing a catalyst according to the above item (26) or (27), wherein the lower end of the chain substance is positioned 1 to 100 cm above the upper end of the catalyst layer packed in the reaction tubes.

(29) The method for packing a catalyst according to any one of the above items (26) to (28), wherein the catalyst is a catalyst for producing acrylic acid or methacrylic acid.

(30) The method for packing a catalyst according to any one of the above items (26) to (29), wherein a size of the reaction tubes of the fixed bed multi-tube reactor is 2 to 10 m in length and 50 mm or less in diameter.

Hereinafter, the first invention of the present invention will be described in detail.

The first invention involves a method for vapor phase catalytic oxidation using a fixed bed multi-tube heat-exchanger type reactor provided with a plurality of reaction tubes.

In other words, a reaction product gas is produced in the reactor by circulating a heating medium outside the reaction tubes and feeding a raw material gas inside the reaction tubes packed with a catalyst.

According to the first invention, the heating medium is preferably used for absorbing heat of reaction generated from the reaction tubes. Any material can be used for the heating medium as long as the material has a function of absorbing the heat of reaction generated from the reaction tubes. Examples of the heating medium include: organic heating media such as partially-hydrogenated triphenyl; and inorganic molten salts such as alkali metal (sodium, potassium, or the like) nitrate or nitrite, so-called niter.

Further, according to a method for vapor phase catalytic oxidation of the first invention, the raw material gas or the catalyst can be appropriately selected in accordance with a desired type of the reaction product gas.

A vapor phase catalytic oxidation reaction of the first invention is a method widely used for producing (meth)acrolein or (meth)acrylic acid from propane, propylene, or isobutylene in the presence of a mixed oxide catalyst using molecular oxygen or a molecular oxygen-containing gas.

The method generally involves: producing acrylic acid through vapor phase oxidation of propane using an Mo—V—Te mixed oxide catalyst, an Mo—V—Sb mixed oxide catalyst, or the like; or producing (meth)acrylic acid by oxidizing propylene or isobutylene in the presence of an Mo—Bi mixed oxide catalyst to mainly produce (meth)acrolein in a former reaction and by oxidizing the (meth)acrolein produced in the former reaction in the presence of an Mo—V mixed oxide catalyst.

Examples of typical systems of commercialized methods for vapor phase catalytic oxidation include a one-pass system, an unreacted propylene recycle system, and a flue gas recycle system. Hereinafter, the systems will be descried using propylene as an example.

The one-pass system involves: mixing and feeding propylene, air, and steam from a raw material gas inlet of the respective reaction tubes of a fixed bed multi-tube reactor for a former reaction; converting the raw material gas to mainly acrolein and acrylic acid; feeding an outlet gas into the reaction tubes of a fixed bed multi-tube reactor for a latter reaction without separating products from the outlet gas; and oxidizing the acrolein to acrylic acid. At this time, a general method also involves feeding air and steam required for a reaction in the latter reaction to the latter reaction in addition to the former reaction outlet gas.

The unreacted propylene recycle system for recycling a part of the unreacted propylene involves: guiding the reaction product gas containing acrylic acid obtained from an outlet of the latter reactor to an acrylic acid collecting device; collecting the acrylic acid in an aqueous solution; and feeding a part of waste gas containing the unreacted propylene from the collecting device to the raw material gas inlet of the former reaction.

The flue gas recycle system involves: guiding the reaction product gas containing acrylic acid obtained from the outlet of the latter reactor to the acrylic acid collecting device; collecting the acrylic acid in an aqueous solution; catalytically combusting and oxidizing all waste gas from the collecting device; converting the unreacted propylene or the like in the waste gas to mainly carbon dioxide and water; and adding a part of the obtained flue gas to the raw material gas inlet of the former reaction.

The catalyst in the method for vapor phase catalytic oxidation of the first invention is preferably used for packing of the catalyst for acrylic acid formation to the reaction tubes of the fixed multi-tubular reactor used for forming (meth)acrolein or (meth)acrylic acid. Specific examples of the catalyst include the following.

Examples of the catalyst used for a vapor phase catalytic oxidation reaction for forming (meth)acrylic acid or (meth)acrolein include a catalyst used in the former reaction for converting an olefin into unsaturated aldehyde or unsaturated acid and a catalyst used in the latter reaction for converting the unsaturated aldehyde into the unsaturated acid. Those catalysts can be employed to either reaction according to the first invention.

The following formula (I) represents an example of the catalyst used for the former reaction.

$$Mo_a W_b Bi_c Fe_d A_e B_f C_g D_h E_i O_x \qquad (I)$$

(wherein, Mo represents molybdenum; W represents tungsten; Bi represents bismuth; Fe represents iron; A represents at least one type of element chosen from nickel and cobalt; B represents at least one type of element selected from the group consisting of sodium, potassium, rubidium, cesium, and thallium; C represents at least one type of element selected from alkali earth metals; D represents at least one type of element selected from the group consisting of phosphorus, tellurium, antimony, tin, cerium, lead, niobium, manganese, arsenic, boron, and zinc; E represents at least one type of element selected from the group consisting of silicon, aluminum, titanium, and zirconium; O represents oxygen; a, b, c, d, e, f, g, h, i, and x represent atomic ratios of Mo, W, Bi, Fe, A, B, C, D, E, and O respectively; and if a=12, $0 \leq b \leq 10$, $0 < c \leq 10$ (preferably $0.1 \leq c \leq 10$), $0 < d \leq 10$ (preferably $0.1 \leq d \leq 10$), $2 \leq e \leq 15$, $0 < f \leq 10$ (preferably $0.001 \leq f \leq 10$), $0 \leq g \leq 10$, $0 \leq h \leq 4$, and $0 \leq i \leq 30$; and x is a value determined from oxidation states of the respective elements.)

The following formula (II) represents an example of the catalyst used for the latter reaction of the first invention.

$$Mo_a V_b W_c Cu_d X_e Y_f O_g \qquad (II)$$

(wherein, Mo represents molybdenum; V represents vanadium; W represents tungsten; Cu represents copper; X represents at least one type of element selected from the group consisting of Mg, Ca, Sr, and Ba; Y represents at least one type of element selected from the group consisting of Ti, Zr, Ce, Cr, Mn, Fe, Co, Ni, Zn, Nb, Sn, Sb, Pb, and Bi; O represents oxygen; a, b, c, d, e, f, and g represent atomic ratios of Mo, V, W, Cu, X, Y, and O; if a=12, $2 \leq b \leq 14$, $0 \leq c \leq 12$, $0 < d \leq 6$, $0 \leq e \leq 3$, and $0 \leq f \leq 3$; and g is a value determined from oxidation states of the respective elements.)

The above catalysts can be prepared, for example, through a method disclosed in JP 63-054942 A.

The reaction tubes used in the method for vapor phase catalytic oxidation of the first invention are packed with the catalyst and, as appropriately, an inert substance for dilution of the catalyst (hereinafter, may be referred to as "diluent"). According to the first invention, the catalyst used may be a single catalyst or a catalyst diluted with the inert substance.

Further, packing specifications of the catalyst in the reaction tubes may be determined comprehensively in view of respective factors such as a catalyst type, a catalyst amount, a catalyst form (shape, size), a dilution method for the catalyst (diluent type, diluent amount), and lengths of reaction zones.

The form (shape, size) of the catalyst used in the method for vapor phase catalytic oxidation of the first invention is not particularly limited, and a molding method for the catalyst is also not particularly limited. A molded catalyst molded through an extrusion molding method or a tablet compression method can be used, for example. In addition, a supported catalyst structured as a mixed oxide composed of a catalytic component supported on an inert support such as silicon carbide, alumina, zirconium oxide, and titanium oxide may be used.

Further, the shape of the catalyst may be any shape such as spherical, columnar, cylindrical, ring-shaped, star-shaped, and amorphous. Use of a ring catalyst, in particular, is effective for preventing thermal storage in hot spot portions.

Further, any type of the diluent may used as long as it is stable under conditions of a (meth)acrolein and (meth)acrylate oxidation reaction and is not reactive with raw materials such as olefins and products such as unsaturated aldehydes and unsaturated fatty acids. Specific examples of the diluent include compounds used for catalyst supports such as alumina, silicon carbide, silica, zirconium oxide, and titanium oxide. Further, a form of the diluent, similar to the catalyst, is not limited and may be any shape such as spherical, columnar, ring-shaped, a small piece, a net, and amorphous. The inert substance is used for adjusting activity of the whole catalyst in a packed layer to prevent abnormal heat generation during an exothermic reaction.

The amount of the inert substance is suitably determined depending on an expected catalyst activity. Further, the packing specifications of the catalyst may differ by layers of reaction zones of one reaction tube. For example, packing specifications of the catalyst packed in an upper portion of a reaction tube may differ from the packing specifications of the catalyst packed in a lower portion of the reaction tube. Generally, the number of the reaction zones are preferably set to 2 to 3 within one reaction tube.

Further, a preferable method involves, for example: dividing the packed layer of the reaction tubes; lowering the catalyst activity and increasing the amount of the inert substance used to suppress the heat generation near the raw material gas inlet; and enhancing the catalyst activity and reducing the amount of the inert substance used to accelerate the reaction near the raw material gas outlet.

According to the first invention, the fixed bed multi-tube heat-exchanger type reactor is generally used industrially and is not particularly limited.

Next, the pressure loss of the reaction tubes in the method for vapor phase catalytic oxidation of the first invention will be described.

The first invention relates to the method for vapor phase catalytic oxidation for producing (meth)acrolein, (meth)acrylic acid, and the like, in which the pressure losses of the respective reaction tubes after packing the catalyst in the fixed bed multi-tube heat-exchanger type reactor for a vapor phase oxidation reaction is made uniform. The first invention more specifically relates to the method for vapor phase catalytic oxidation, characterized in that the pressure losses of the respective reaction tubes after catalyst packing is adjusted within ±20% of an average pressure loss of the reaction tubes by: packing an inert substance at the raw material gas inlet portion of the reaction tubes or removing and re-packing the catalyst packed, for a reaction tube having a pressure loss lower than the average pressure loss of the reaction tubes; and removing and re-packing the catalyst packed, for a reaction tube having a pressure loss higher than the average pressure loss of the reaction tubes.

Here, the average pressure loss of the reaction tubes is an average value of the pressure loss of 0.5% or more, preferably 1% or more of the reaction tubes randomly selected from the total reaction tubes.

The fixed bed multi-tube reactor used for vapor phase catalytic oxidation of propane, propylene, or the like is provided with several thousands to several ten thousands of the reaction tubes, and it is very difficult to uniform packed states of the catalyst in all of the reaction tubes. In other words, catalyst powdering or degradation is hardly made uniform in the respective reaction tubes during catalyst packing. Further, catalyst packing time of the respective reaction tubes is hardly made equal. The packed state of the catalyst, that is the pressure loss, which becomes a particularly important factor in the oxidation reaction, differs greatly by the reaction tubes.

To be specific, a problem caused by the difference in the pressure loss involves: changing the amount of gas flowing to the reaction tubes; changing reaction situations by the reaction tubes; and resulting in different reaction situations by the reaction tubes even within the same reactor.

The reaction temperature of the reactor is determined according to an average value of the reaction states of the total reaction tubes. In the former reactor for an oxidation reaction of propylene, for example, propylene conversions vary by the reaction tubes. Therefore, the temperature of the heating medium is determined according to the average propylene conversion of the total reaction tubes. Thus, not all reaction tubes are operated under optimum conditions.

In other words, providing a uniform reaction state of the respective reaction tubes inside the reactor for oxidation reaction, that is the pressure loss, is important for a safe operation of the reactor for oxidation reaction from reasons described below.

(1) The conversion of the raw material substance reduces and the yield decreases in a reaction tube with a large amount of gas at the same reaction temperature. In contrast, an excessive reaction occurs and side reactions increase to reduce selectivity, in a reaction tube with a small amount of gas at the same reaction temperature.

(2) Further, excessive side reactions occur in a reaction tube with a small amount of gas. A reduction of the selectivity combined with an oxygen shortage in an outlet portion of the reaction tube causes not only catalyst deterioration, but also coking.

(3) The reaction situations of the respective reaction tubes differ, so that conditions of the catalyst deterioration differ, thereby reducing the catalyst life as a whole.

According to the first invention, a method of packing the catalyst to the reaction tubes of the fixed bed multi-tube heat-exchanger type reactor is not particularly limited. However, the catalyst is preferably packed while leaving an empty portion in the upper portion of the reaction tubes.

0.5% or more, preferably 1% or more of the reaction tubes are randomly selected from the total reaction tubes after catalyst packing, and the pressure loss is measured. The pressure loss can be measured by passing a gas of a constant flow rate through the reaction tubes using a mass flow meter and measuring the pressure at that time. The gas passed through the reaction tubes at the time is not particularly limited, but air is desirably used for safety reasons. The amount of the gas passed through the reaction tubes is desirably the amount of the gas actually passed through during a reaction at a steady state.

After measuring the pressure losses of the total reaction tubes, the average value of the pressure losses of the measured reaction tubes is calculated. A reaction tube having a pressure loss lower than the average value is packed with an inert substance in an empty portion of the reaction tube or has the catalyst removed and re-packed, to adjust the pressure loss within ±20%, preferably ±10% of the average value.

A reaction tube having a pressure loss higher than the average value by 20% or less has the catalyst removed and re-packed.

If a pressure loss is higher than the average pressure loss of the measured reaction tubes by 20% or more, the amount of the raw material-gas flowing through the reaction tubes reduces, thereby causing an excessive reaction. Further, if a pressure loss is lower by 20% or more, the amount of the raw material gas flowing through the reaction tubes increases, thereby degrading the reactivity.

The respective reaction tubes are generally provided with catalyst holders in lower portions, and the catalyst is packed from upper portions of the reaction tubes. The catalyst of the reaction tubes may be removed by detaching the catalyst holders at the lower portions of the reaction tubes and allowing the catalyst to fall. For a mode in which a plurality of the reaction tubes shares the catalyst holder, the catalyst may be removed from the upper portions using a vacuum pump.

Moreover, according to the first invention, the inert substance added after measuring the pressure loss for particularly adjusting the pressure loss or the inert substance diluting the catalyst re-packed among the inert substance packed-to the above reaction tubes is referred to as an inert substance for adjustment. The inert substance for adjustment is preferably selected from the group consisting of alumina, silicon carbide, silica, zirconium oxide, and titanium oxide as described above. Further, the form of the inert substance for adjustment is not particularly limited, and may be any shape such as spherical, columnar, ring-shaped, and amorphous.

Further, according to the first invention, the packing specifications of the catalyst may be set considering prediction results of the reaction states inside the reaction tubes described later.

Uniforming the pressure losses of the respective reaction tubes is effective for reducing variations of the reaction states by the respective reaction tubes. However, the reaction states mainly concern effects inside the reaction tubes such as the packed states of the catalyst in the reaction tubes, but do not concern effects outside the reaction tubes such as a fluid state of the heating medium and a reactor structure. Therefore, predicting the reaction states inside the reaction tubes considering effects outside the reaction tubes as well and setting the packing specifications of the catalyst so that the predicted reaction states of the respective reaction tubes become uniform further allow reduction in variations of the reaction states by the respective reaction tubes. The effects outside the reaction tubes include existence of places having a low heat removal effect depending on the reaction tubes or on positions in the same reaction tube.

Therefore, when packing the catalyst in the reaction tubes or re-packing the catalyst in the reaction tubes to provide a uniform pressure loss, the reaction states inside the reaction tubes are predicted by measuring the temperature of the catalyst layers in the reaction tubes or conducting a simulation analysis of the fluid state of the heating medium circulating outside the reaction tubes with the heat of reaction inside the reaction tubes using a computer. The packing specifications of the catalyst in the reaction tubes may be determined according to the prediction results so that nonuniformity of the reaction states among the reaction tubes are reduced. A prediction method for the reaction states inside the respective reaction tubes will be described in detail in the following section regarding the second invention.

Further, according to the first invention, use of a catalyst packing method described below for packing the catalyst allows further reduction in variations of the reaction states by respective reaction tubes.

Therefore, when packing the catalyst in the reaction tubes, the catalyst may be packed by being allowed to fall using a funnel having a net in at least a part thereof. Alternatively, the catalyst may be packed by being allowed to fall while interposing a chain substance in the reaction tubes so that a lower end of the chain substance is positioned above an upper end of the catalyst layers. The catalyst packing methods will be further described in detail in the following sections regarding the third invention and the fourth invention.

Hereinafter, the second invention of the present invention will be described in detail.

The second invention, similar to the first invention, involves a method for vapor phase catalytic oxidation using a fixed bed multi-tube heat-exchanger type reactor provided with a plurality of reaction tubes.

According to the second invention, a description regarding a heating medium used is similar to as that regarding the heating medium in the first invention.

Further, descriptions regarding a raw material gas and a catalyst are similar to those described in the section of the first invention.

Here, specific examples of the catalyst which can be used, similar to those of the first invention, preferably include the Mo—Bi mixed oxide catalyst represented by the above formula (1) and the Mo—V mixed oxide catalyst represented by the above formula (2).

The reaction tubes used in the method for vapor phase catalytic oxidation of the second invention are packed with the catalyst and, as appropriately, an inert substance for diluting the catalyst (hereinafter, may also be referred to as "diluent").

The packing specifications of the catalyst to the reaction tubes may be determined comprehensively in view of respective factors such as a catalyst type, a catalyst amount, a catalyst form (shape, size), a dilution method for the catalyst (diluent type, diluent amount), and lengths of reaction zones.

The form (shape, size) of the catalyst used in the method for vapor phase catalytic oxidation of the second invention is similar to that described in the first invention. A molded catalyst or a supported catalyst can be used without any particular limitation, and in addition, a catalyst may be in any shape.

Further, descriptions regarding the diluent type and a mixing ratio of the catalyst and the diluent are similar to those described in the first invention.

Further, a description that the packing specifications of the catalyst may differ by layers of reaction zones within one reaction tube is similar to that described in the first invention.

Next, a prediction method for reaction states inside the respective reaction tubes in the method for vapor phase catalytic oxidation of the second invention will be described.

According to the second invention, the reaction states are predicted for preventing an emergence of reaction tubes in abnormal reaction states such as hot spots departing from a normal reaction state.

Therefore, the reaction tubes in abnormal reaction states, differing from the normal reaction state or the reaction tubes that may be in abnormal reaction states are predicted.

To be specific, reaction tubes that are not in a uniform state (in a reaction state of the same level) with other reaction tubes are selected.

Further, thermal states inside the reaction tubes are preferably grasped for predicting the reaction states.

Measuring temperature of catalyst layers of the reaction tubes or using a computer simulation analysis enables grasping the thermal states inside the reaction tubes.

To be specific, the reaction states different from the reaction states of other reaction tubes can be predicted: when temperature of a reaction tube is judged higher than that of other reaction tubes from results of temperature measurements of the catalyst layers of the reactions tubes; and when temperature inside a reaction tube is judged higher than that inside other reaction tubes from results of computer simulation analysis.

When grasping the thermal states inside the reaction tubes through simulation analysis using a computer, a fluid analysis of the heating medium or an analysis combining the fluid analysis of the heating medium with an analysis of the heat of reaction inside the reaction tubes, to be specific, allows grasping of the thermal states.

The fluid analysis of the heating medium includes: determining a layout of baffles or reaction tubes, a structure of a reactor such as a heating medium feed port, and items regarding the heating medium such as physical properties of the heating medium or a flow through rate of the heating medium; and conducting the simulation. To be specific, a heat-transfer coefficient or a temperature distribution may be computed by calculating a flow direction of the heating medium, a flow rate of the heating medium, or the like using a momentum conservation equation, a mass conservation equation, an enthalpy conservation equation, or the like. According to the second invention, CFX (United Kingdom, CFX Ltd.) can be used for the analysis as a fluid analysis software.

Further, the analysis of the heat of reaction inside the reaction tubes includes: determining items regarding the reaction tubes such as structures of the reaction tubes, physical properties of feed gas and the catalyst, a rate equation, or the like; and conducting the simulation. To be specific, a reaction level may be determined at respective minute zones inside the reaction tubes using a momentum conservation equation, a mass conservation equation, an enthalpy conservation equation, a rate equation, or the like. According to the second invention, g-PROMS (United Kingdom, AEA Technology plc) can be used for the analysis as an analysis software.

As described above, further incorporating the analysis of the heat of reaction inside the reaction tubes by considering portions of poor heat removal using the fluid analysis of the heating medium enables prediction of the reaction states inside the respective reaction tubes in all places inside the reactor.

The inventors of the present invention have confirmed as a result of the simulation analysis using a computer in a method for vapor phase catalytic oxidation using a fixed bed multi-tube heat-exchanger type reactor of a double segment type shown below in FIG. 2 or a fixed bed multi-tube heat-exchanger type reactor of a ring and doughnut type shown below in FIG. 3 that: the heat removal of a flow along the reaction tubes (vertical flow) is worse than that of the flow perpendicular to the reaction tubes (horizontal flow); and the heat removal of the vertical flow in a central portion of the reactor is much worse than that of the vertical flow of an outer peripheral portion of the reactor.

Further, increase of the flow through rate of the heating medium in the fixed bed multi-tube heat-exchanger type reactors was confirmed to improve the heat removal effect in accordance with the flow through rate of the heating medium of a horizontal flow. However, the increase of the flow through rate of the heating medium did not improve the heat removal effect in a portion of the heating medium of a vertical flow, particularly in a portion of the heating medium of a vertical flow in a central portion of the reactor despite the increase.

Further, an existence of a portion of poor heat removal was confirmed in a residence portion of the heating medium in an outer peripheral portion of the reactor according to a method for vapor phase catalytic oxidation using a fixed bed multi-tube heat-exchanger type reactor of a multi-baffle type of FIG. 4.

Therefore, the portions of poor heat removal are preferably sufficiently considered to carefully predict the reaction states of the reaction tubes in those portions.

Then, according to the second invention, the packing specifications of the catalyst in the respective reaction tubes are changed in accordance with the prediction results based on the above prediction results.

In other words, the packing specifications of the catalyst are changed so that the reaction tubes judged to have different reaction states from the other reaction tubes described above are brought into the same reaction states as in the other reaction tubes. That is, the packing specifications of the catalyst are changed so that nonuniformity of the reaction states is reduced among the reaction tubes.

For example, the packing specifications of the catalyst are changed for a reaction tube judged to have a temperature departing from a given catalyst layer temperature range, revealed from the temperature measurement of the catalyst layers in the reaction tubes. The packing specifications are changed so that the reaction tube has a catalyst layer temperature of the same level as those of the other reaction tubes.

Alternatively, as a result of the simulation analysis using a computer, the packing specifications of the catalyst are changed for a reaction tube in a portion of a poor circulating state of the heating medium, which is a reaction tube judged to have a temperature departing from a given temperature range because of inefficient heat removal of the heat of reaction generated in the reaction tube. The packing specifications are changed so that the reaction tube has a temperature of the same level as the presumed temperature inside other reaction tubes.

A rough standard for the change in the packing specifications will be described below. For example, peak temperatures of the catalyst layers of the respective reaction tubes are determined through the temperature measurement or the simulation. Next, an average value of the peak temperatures representing a whole reactor is determined based on the results of the respective peak temperatures. Then, the average value of the peak temperatures and the peak temperatures of the respective reaction tubes are compared. The packing specifications are changed for the reaction tubes having a temperature difference of 15° C. or more, preferably 10° C. or more, with the average peak temperature. Here, the peak temperatures of the catalyst layers refer to temperatures of portions having the highest temperatures when the catalyst is packed in the reaction tubes in single layers. The peak temperatures of the catalyst layers refer to temperatures of portions having the highest temperatures in respective reaction zones when the catalyst is packed in several reaction zones. Further, the average peak temperature is calculated as an average value of the peak temperatures of the reaction tubes disregarding temperatures of portions of remarkably poor heat removal.

According to the second invention, the packing specifications of the catalyst can be changed considering the respective factors such as a catalyst type, a catalyst amount, a catalyst form (shape, size), a dilution method for the catalyst (diluent type, diluent amount), and lengths of reaction zones. Of those, the packing specifications may be preferably changed by changing the amounts of the catalyst and the diluent to adjust the mixing ratio of the catalyst and the diluent.

According to the second invention, the packing specifications may be preferably changed to reduce the temperatures inside the catalyst layers in the reaction tubes, that is, to a direction of suppressing the reaction.

Note that, according to the method for vapor phase catalytic oxidation of the second invention, feeding a large amount of the raw materials for increasing the productivity may result in places of heat removal slower than the increase of the heat of reaction even in places where the heat generation and the heat removal were balanced. In such a case, the packing specifications of the catalyst in the reaction tubes are changed. In addition, it is effective to stop feed of the raw material gas to the reaction tubes of extremely poor heat removal portions by plugging or the like to prevent the flow of the gas.

As described above, when setting the packing specifications of the catalyst according to the first invention, variations of the reaction states by the respective reaction tubes can be reduced by: predicting the reaction states inside the reaction tubes according to the second invention; and setting the packing specifications of the catalyst in the reaction tubes in accordance with the prediction results so that nonuniformity of the reaction states among the reaction tubes is reduced.

In other words, the present invention provides, as a more preferable mode of the first invention, a method for vapor phase catalytic oxidation characterized by: predicting the reaction states inside the reaction tubes by measuring the catalyst layer temperature of the reaction tubes or conducting the simulation analysis of the fluid state of the heating medium circulating outside the reaction tubes and the heat of reaction inside the reaction tubes using a computer; and determining the packing specifications of the catalyst in the reaction tubes in accordance with the prediction results so that nonuniformity of the reaction states among the reaction tubes is reduced when packing the catalyst in the reaction tubes according to the first invention. Here, the items determining the packing specifications of the catalyst are as described in the section of the first invention or the second invention.

Hereinafter, the third invention of the present invention will be described in detail.

A catalyst packing method according to the third invention of the present invention is a catalyst packing method involving packing of the catalyst while removing the powdered or degraded catalyst or the like using a funnel having a net in at least a part thereof.

A net mesh of the funnel is smaller than the outer diameter of the catalyst or the like for separating and removing the catalyst or the like powdered or degraded by vibration or impact during transfer, transport, and handling of the catalyst.

A form, a material, and a size of the funnel are not particularly limited as long as a part of the funnel consists of a net and the funnel has a structure not allowing the powdered or degraded catalyst to enter from the net portion into the reaction tubes.

An inclined portion of the funnel may be provided with a wire net, a punching metal, or the like for providing a funnel consisting of a net in at least a part thereof.

FIG. 6(a) shows a preferable form of the funnel, and an inclined portion of a funnel 21 is provided with a net mesh 22. An angle of the inclination is preferably 10 to 75°, more preferably 30 to 50°. If the angle of the inclination is 10° or less, the catalyst or the like may undesirably reside in the funnel or in a wire net portion. If the angle of the inclination is 75° or more, separation of the powdered or degraded catalyst or the like may undesirably become incomplete because of excessive inclination.

The mesh portion is preferably provided to position outside a diameter of the reaction tubes, or a recovery bag (or recovery container) 23 is provided to cover the mesh portion 22 for preventing the powdered or degraded catalyst or the like from entering the reaction tubes of the fixed bed multi-tube reactor.

Further, FIGS. 6(b) and (c) respectively are plan views seen from an A direction and B direction of FIG. 6(a), showing an example of a funnel size in mm units.

Examples of the funnel material include tinplate, stainless steel, and plastic. The funnel size is suitably selected depending on a size of the reaction tubes of the fixed bed multi-tube reactor.

The funnel may have a general form composed of a conical portion and a straight pipe portion. However, the funnel used is preferably a half funnel having a perpendicular side and a partially conical side, and a diameter of the straight pipe portion is smaller than an inner diameter of the reaction tubes at least in a portion where the funnel is inserted into the reaction tubes. Further, the funnel is preferably provided with a wire net on an inclined side of the partial cone and with a powder reservoir for receiving fine powders passing through the net.

The funnel preferably has a size of a sufficient length for separating or removing the powdered or degraded catalyst or the like using the wire net provided on the inclined side of the partial cone within a range not effecting workability.

According to the third invention, the fixed bed multi-tube reactor is generally used industrially and is not particularly limited as described in the sections of the first invention and the second invention.

A description regarding the catalyst used in the third invention is similar to that in the section of the first invention. Here, specific examples of the catalyst which can be used, similar to those described in the first invention, preferably include an Mo—Bi mixed oxide catalyst represented by the above formula (1) and an Mo—V mixed oxide catalyst represented by the above formula (2).

According to the third invention, the catalyst used may also be a single catalyst or a catalyst diluted with an inert substance, similar to that in the first invention or the second invention.

The form of the catalyst (shape, size) used in the method for vapor phase catalytic oxidation of the third invention is similar to that described in the first invention or the like. A molded catalyst or a supported catalyst may be used without any particular limitation. Further, the catalyst may be in any shape.

Further, the descriptions regarding a type and a form of the inert substance or an amount of the inert substance used are similar to those in the first invention.

Further, the packing specifications of the catalyst may differ by layers of reaction zones in one reaction tube as described in the first invention.

The catalyst packing method of the third invention more preferably involves purging the reaction tubes with dry air or the like for removing the powdered product of the catalyst generated inside the reaction tubes. The reaction tubes are packed with the catalyst while removing the powdered or degraded catalyst using a funnel with a net in at least a part thereof.

As described above, when packing the catalyst according to the first invention, the variations of the reaction states by the respective reaction tubes can be eliminated by packing the catalyst according to the packing method of the third invention.

In other words, the present invention, as a more preferable mode of the first invention or of a combination of the first invention and the second invention, provides a method of packing the catalyst by allowing the catalyst to fall using a funnel with a net in at least a part of the funnel when packing the catalyst in the reaction tubes according to the first invention.

Hereinafter, the fourth invention of the present invention will be described in detail.

According to the fourth invention, the fixed bed multi-tube reactor is generally used industrially and is not particularly limited as described in the section of the first invention and the second invention. The fixed bed multi-tube reactor of the fourth invention particularly preferably has reaction tubes with a length of 2 to 10 m and a diameter of 50 mm or less.

A description regarding the catalyst used in the fourth invention is similar to that in the section of the first invention. Here, specific examples of the catalyst which can be used, similar to those described in the first invention, preferably include an Mo—Bi mixed oxide catalyst represented by the above formula (1) and an Mo—V mixed oxide catalyst represented by the above formula (2).

According to the fourth invention, the catalyst used may be a single catalyst or a catalyst diluted with an inert substance, similar to that in the first invention or the second invention.

The form of the catalyst (shape, size) used in the method for vapor phase catalytic oxidation of the fourth invention is similar to that described in the first invention or the like. A molded catalyst or a supported catalyst may be used without any particular limitation. Further, the catalyst may be in any shape.

Further, the descriptions regarding a type and a form of the inert substance or an amount of the inert substance used are similar to those in the first invention.

The chain substance interposing inside the reaction tubes according to the fourth invention is not particularly limited as long as the substance has a thickness or is a material which reduces a falling speed of the catalyst and does not substantially disturb the falling of the catalyst. Specific examples of the chain substance include chains of stainless steel, plastic, or the like and may be a substance which does not damage or break from contact with the falling catalyst. The thickness of the chain substance may be suitably selected from the number of the chain substances used and the size of the reaction tubes.

FIG. 8 shows an example of the chain substance having a ring outer diameter of 6 mm×9 mm used in the present invention. A preferable chain substance includes chains composed of an oval ring member having a ring wire diameter of 1 to 1.5 mm and a ring outer diameter of 5 to 15 mm. A wire diameter of less than 1 mm, lacking in strength may result in break of the chain during use. On the other hand, a wire diameter of more than 1.5 mm easily results in winding of the chain to form a "cluster". The ring outer diameter is preferably within the above range for easy handling. If a joint exists in the ring member, the joint is preferably welded.

According to the fourth invention, the number of the chain substances used for interposing inside the reaction tubes is at least one. The larger the number, the larger the effect is for suppressing the powdering or the degradation of the catalyst during catalyst packing. However, an excess number may hinder the catalyst from falling, and thus, the number may be suitably selected from the thickness of the chain substance, the size of the reaction tubes, or the like.

The length of chain substance may be provided so that a lower end of the chain substance is positioned 1 to 100 cm, preferably 1 to 50 cm, and more preferably 5 to 20 cm above an upper end of a catalyst layer packed in the reaction tubes.

According to the fourth invention, the packing specifications of the catalyst are not particularly limited. However, multi-layer packing is preferable for changing activity of the catalyst packed inside the reaction tubes to increase reaction efficiency of a target reaction using the reaction tubes packed with the catalyst.

The multi-layer packing provides several catalyst layers by dividing the packed layers of the reaction tubes to change the activity of the catalyst packed inside the reaction tubes. In such a case, the catalyst is preferably packed inside the reaction tubes by preparing a chain substance with an adjusted length for each of the catalyst layers and changing to an adequate chain substance when packing the target catalyst layer.

An interposing means for the chain substance inside the reaction tubes includes a method of hanging the chain substance on a packing funnel provided on an upper portion of the reaction tubes. A specific example of the method, as shown in FIGS. 7(a) to (c), involves: welding in a cross a stainless steel linear member 32 to a stainless steel (SUS304, for example) ring 31 having a larger diameter than that of a reaction tube so that the chain substance does not fall inside the reaction tube; and fixing a chain 33 to the cross portion using a stainless steel wire.

As described above, when packing the catalyst according to the first invention, the variations of the reaction states by the respective reaction tubes can be eliminated by packing the catalyst according to the packing method of the fourth invention.

In other words, the present invention, as a more preferable mode of the first invention or of a combination of the first invention and the second invention, provides a method of packing the catalyst by allowing the catalyst to fall by interposing the chain substance inside the reaction tubes so that the lower end of the chain substance is positioned above the upper end of the catalyst layer when packing the catalyst in the reaction tubes according to the first invention.

BEST MODE FOR CARRYING OUT THE INVENTION

Figure 1:
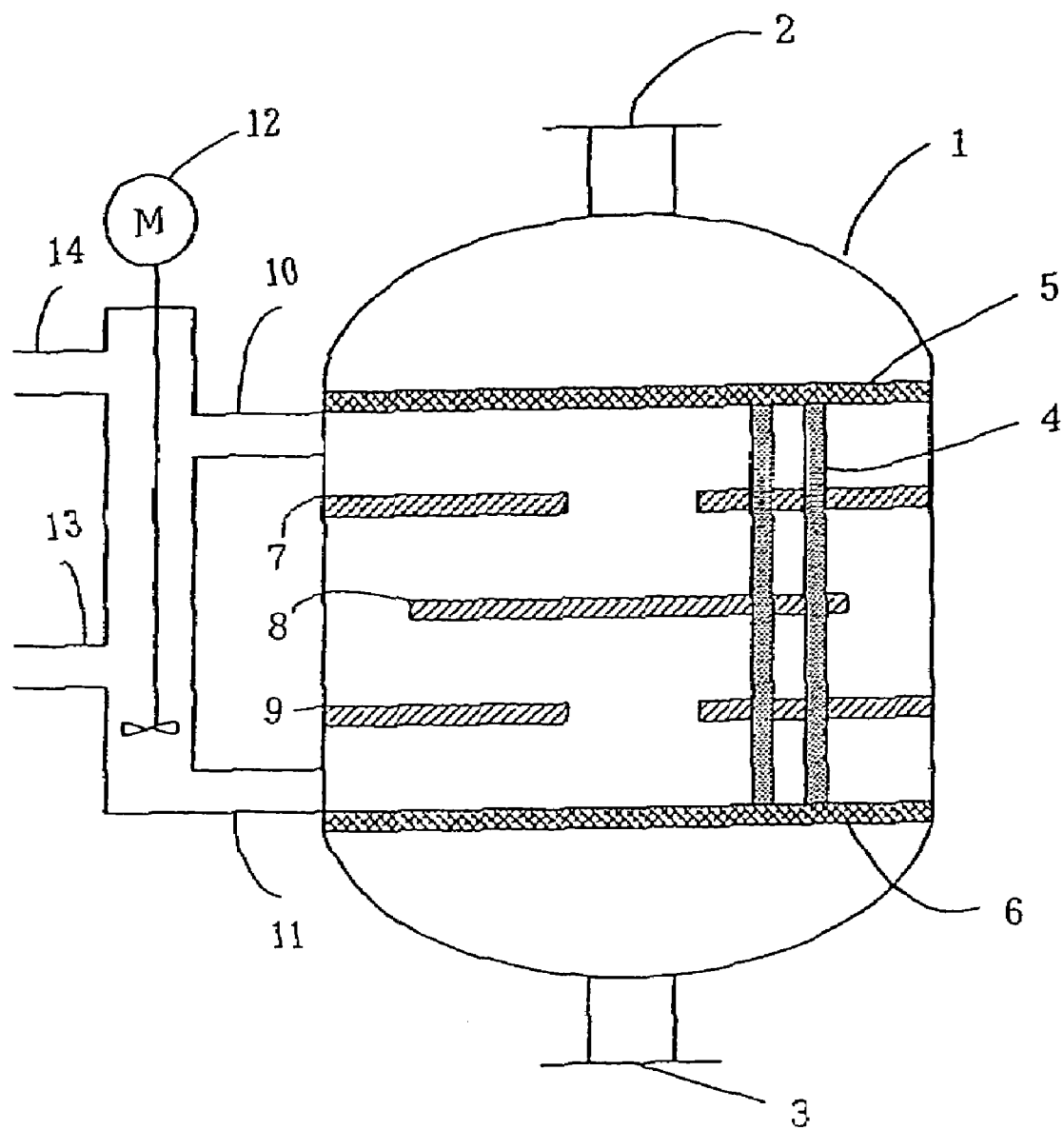
FIG. 1 is a diagram of a mode of a fixed bed multi-tube heat-exchanger type reactor used in the present invention.

Hereinafter, the present invention will be further described in detail by way of examples and comparative examples, but the present invention is not limited by the examples so long as not departing from the scope of the invention.

<First Invention>

<Standard Conditions>

Reaction Tubes of a Fixed Bed Multi-Tube Heat-Exchanger Type Reactor

A pilot device of a fixed bed reactor consists of a reaction tube which has an inner diameter of 27 mm and a length of 5 m and is provided with a jacket for a heating medium. The pilot device can uniformly control temperature using niter as the heating medium.

Former Reaction Catalyst (Ppropylene Vapor Phase Catalytic Oxidation Catalyst)

A catalyst of the following composition (atomic ratio) was prepared by a method disclosed in JP 63-054942 A as the propylene vapor phase catalytic oxidation catalyst.

$Mo:Bi:Co:Fe:Na:B:K:Si:O=12:1:0.6:7:0.1:0.2:0.1:18:X$

Wherein, X is a value determined from oxidation states of respective metal elements.

The reaction tube was packed with 0.86 L of the catalyst, 0.43 L of a mixture containing 70% of the catalyst and 30% of alumina balls in volume ratio thereon, and 0.43 L of a mixture containing 50% of the catalyst and 50% of the alumina balls in volume ratio further thereon.

Former Reaction Conditions

A raw material gas having a composition of 9.5 mol% of propylene, 71.9 mol% of air, and 18.6 mol% of steam was fed to the reaction tube of the fixed bed multi-tube reactor of the pilot device or an actual equipment at a flow rate of 1,032 NL/H.

Reaction Pressure

An outlet pressure of a latter reactor was adjusted to 50 KPaG (gauge pressure).

EXAMPLE 1

A pressure loss of the reaction tube when feeding air of the same volume (1,032 NL/H) as the volume of gas fed under the standard reaction conditions was 7.1 KPa after packing the former catalyst in the reaction tube of the pilot device under standard conditions.

Further, reaction performance of the reaction tube at a reaction temperature of 323° C. resulted in propylene conversion of 98.0% and total yield of acrylic acid and acrolein of 92.1%. (Here, the reaction temperature can also be referred to as "heating medium temperature" because the reaction temperature can be determined from the temperature of the heating medium circulating outside the reaction tube for absorbing heat of reaction generated from the reaction tube.)

COMPARATIVE EXAMPLE 1

The catalyst was packed following the same method as in Example 1 except that catalyst packing time was changed. As a result, the pressure loss of the reaction tube after catalyst packing was 5.6 KPa, and the volume of air increased to reach the same pressure loss of 7.1 KPa as in Example 1 was 1,200 NL/H.

The reaction was conducted at a heating medium temperature of 323° C. following the same method as in Example 1 except that the gas volume fed to the former reaction tube was changed to 1,200 NL/H. The propylene convention was 96.7% and the total yield of the acrylic acid and the acrolein was 90.1%, resulting in a very low conversion compared to Example 1.

COMPARATIVE EXAMPLE 2

The catalyst was packed following the same method as in Example 1 except that catalyst packing time was changed. As a result, the pressure loss of the reaction tube after catalyst packing was 8.4 KPa, and the volume of air decreased to reach the same pressure loss of 7.1 KPa as in Example 1 was 920 NL/H.

The reaction was conducted at a heating medium temperature of 323° C. following the same method as in Example 1 except that the gas volume fed to the former reaction tube was changed to 920 NL/H. The propylene conversion was 98.8% and the total yield of the acrylic acid and the acrolein was 91.6%, resulting in an excessive oxidation reaction.

EXAMPLE 2

Alumina balls as an inert substance were packed into the reaction tube of Comparative Example 1, so that the pressure loss of the reaction tube was 7.1 KPa, the same as in Example 1, when feeding air of the same volume (1,032 NL/H) as the volume of gas fed under the standard reaction conditions. The gas volume fed to the former reactor was 1,302 NL/H, and the reaction was conducted under the same conditions as in Example 1 at a heating medium temperature of 323° C. As a result, the propylene conversion was 97.9% and the total yield of the acrylic acid and the acrolein was 92.0%, substantially the same result as in Example 1.

Table 1 collectively shows results of Examples 1 and 2 and Comparative Examples 1 and 2.

TABLE 1

| | Pressure loss after catalyst packing (KPa) | With or without correction of catalyst packing specification for adjusting pressure loss | Reaction temperature (° C.) | Propylene conversion (%) | Total yield of acrolein and acrylic acid (%) |
|---|---|---|---|---|---|
| Example 1 | 7.1 | Without correction | 323 | 98.0 | 92.1 |
| Comparative Example 1 | 5.6 | Without correction | 323 | 96.7 | 90.1 |
| Comparative Example 2 | 8.4 | Without correction | 323 | 98.8 | 91.6 |
| Example 2 | 5.6 | With correction | 323 | 97.9 | 92.0 |

EXAMPLES 3 TO 5 AND COMPARATIVE EXAMPLES 3 AND 4

Effects of the pressure loss on the catalyst over time after catalyst packing were determined using the actual equipment. The actual equipment was a fixed bed multi-tube exchanger reactor having 15,000 reaction tubes. The reaction conditions were basically the same as in Example 1, and an average volume of the gas fed per reaction tube was 1,250 NL/H.

8 reaction tubes packed with a catalyst in different packed states were prepared by changing the catalyst packing time and the catalyst packing method, for Examples 3 to 5 and Comparative Examples 3 and 4, respectively.

Table 2 shows the pressure loss of the reaction tubes after catalyst packing and the pressure loss 1 year after start of the operation. Further, the pressure losses of the 150 reaction tubes of the reactor were measured. The results showed that an average pressure loss was 8.5 KPa, the same value as the pressure loss of the reaction tube in Example 3.

Table 2 also shows the pressure loss of the reaction tubes after catalyst packing and the pressure loss 1 year after the start of the operation in Examples 4 and 5 and Comparative Examples 3 and 4.

The volume of gas flowing through the reaction tubes having a pressure loss higher than the average pressure loss was smaller than the volume of the gas flowing in the reaction tubes having the average pressure loss. As a result, an excessive reaction occurred, not only causing catalyst deterioration, but also becoming a cause of coking. In Comparative Example 3 and Comparative Example 4, outlet portions of the reaction tubes were black, causing coking, and completely blocked. In other words, the reaction tubes were causing yield reduction at the beginning of coking and were completely clogged ultimately, to result in the reaction tubes not being used effectively for the oxidation reaction.

TABLE 2

| | Pressure loss after catalyst packing (KPa) | With or without correction of catalyst packing specification for adjusting pressure loss | Difference with average pressure loss (%) | Pressure loss after 1 year operation (KPa) |
|---|---|---|---|---|
| Example 3 | 8.5 | Without correction | 0 | 8.6 |
| Example 4 | 9.4 | Without correction | +10 | 9.8 |
| Example 5 | 10.2 | Without correction | +20 | 11.2 |
| Comparative Example 3 | 11.1 | Without correction | +30 | Not measurable |
| Comparative Example 4 | 10.6 | Without correction | +24 | Not measurable |

<Second Invention>

FIG. 1 shows a first embodiment mode of the fixed bed multi-tube heat-exchanger type reactor used in a method for vapor phase catalytic oxidation of the second invention.

FIG. 1 shows: a reactor 1; a raw material gas introducing port (for a downflow case) or a reaction product gas discharging port (for an upflow case) 2; a reaction product gas discharging port (for a downflow case) or a raw material gas introducing port (for an upflow case) 3; a reaction tube (catalyst packed inside) 4; an upper tube plate 5; a lower tube plate 6; baffles 7, 8, and 9; a heating medium outlet nozzle 10; a heating medium inlet nozzle 11; a heating medium inlet line for reaction temperature adjustment 13; and a heating medium overflow line 14.

Note that the fixed bed multi-tube heat-exchanger type reactor in FIG. 1 has a for case of structure passing the heating medium in an upflow direction, but the heating medium can be obviously passed in a downflow direction as well according to the present invention.

The raw material gas is mixed with air and/or a diluent gas, a recycle gas, or the like, introduced from the raw material gas introducing port (2 or 3) to the reactor (1), and fed to the reaction tube (4) where the catalyst is packed. The reaction product gas produced by oxidation through a catalytic oxidation reaction inside the reaction tube or an unreacted gas is discharged from the reaction product gas discharging port (3 or 2).

The heating medium is introduced from the heating medium inlet nozzle (11) to a reactor shell by a pump (12), passed through inside the reactor shell while removing the heat of reaction generated inside the reaction tube, discharged from the heating medium outlet nozzle (10), and circulated by the pump. Temperature of the heating medium is controlled by introducing a cooling medium from a cooling medium nozzle (13), and the medium introduced from the nozzle (13) is discharged from the heating medium overflow line (14).

Figure 2:
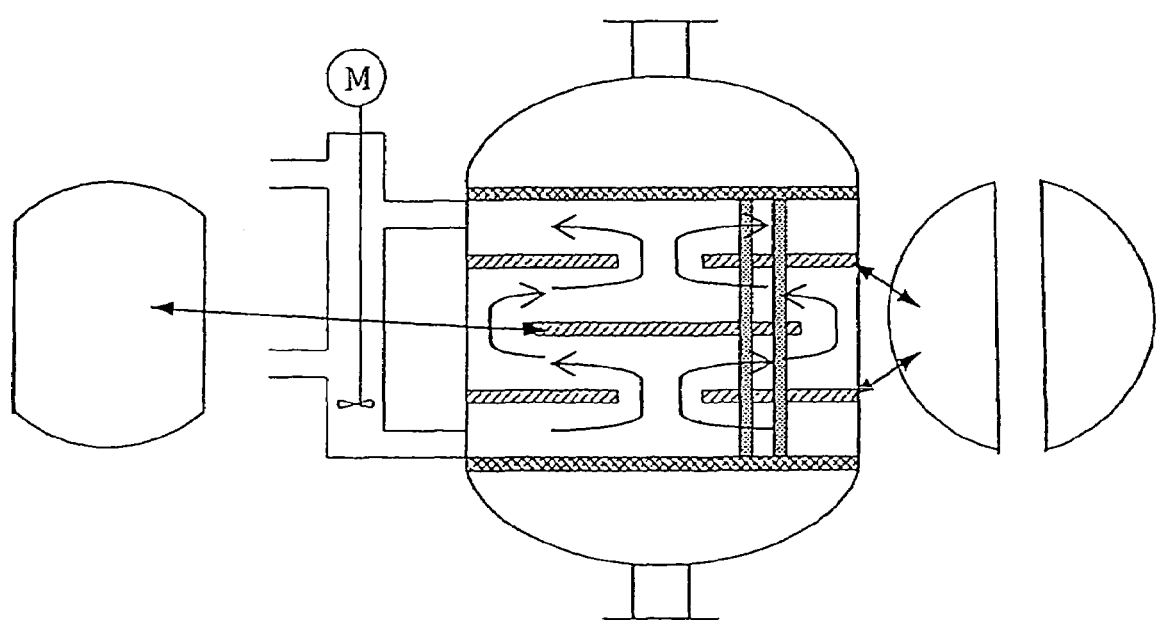
FIG. 2 is a diagram of a mode of a fixed bed multi-tube heat-exchanger type reactor used in the present invention.
Figure 3:
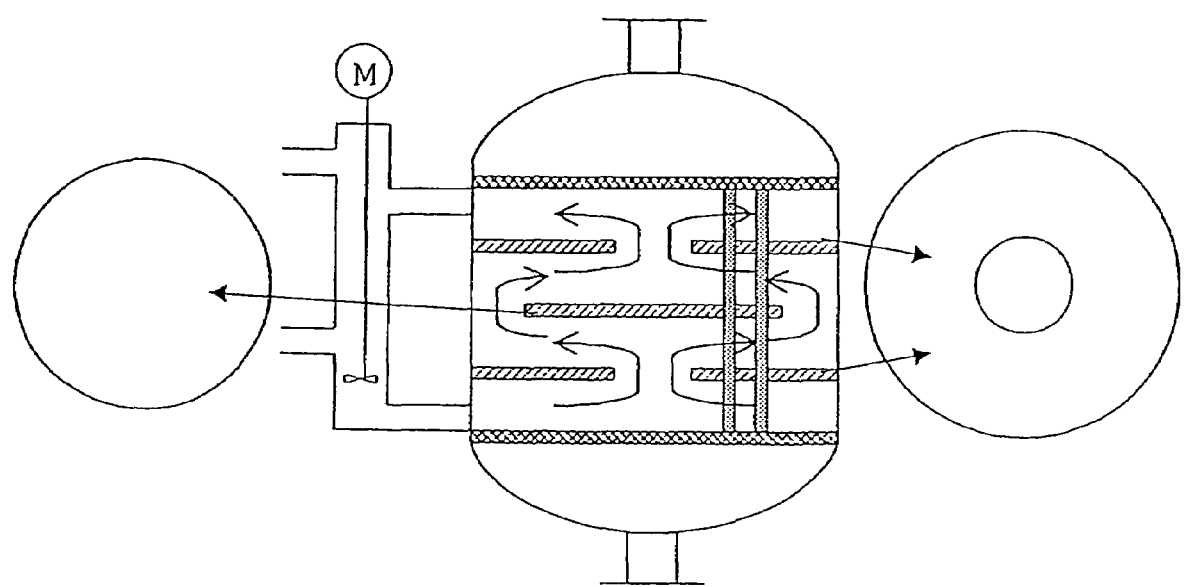
FIG. 3 is a diagram of a mode of a fixed bed multi-tube heat-exchanger type reactor used in the present invention.
Figure 4:
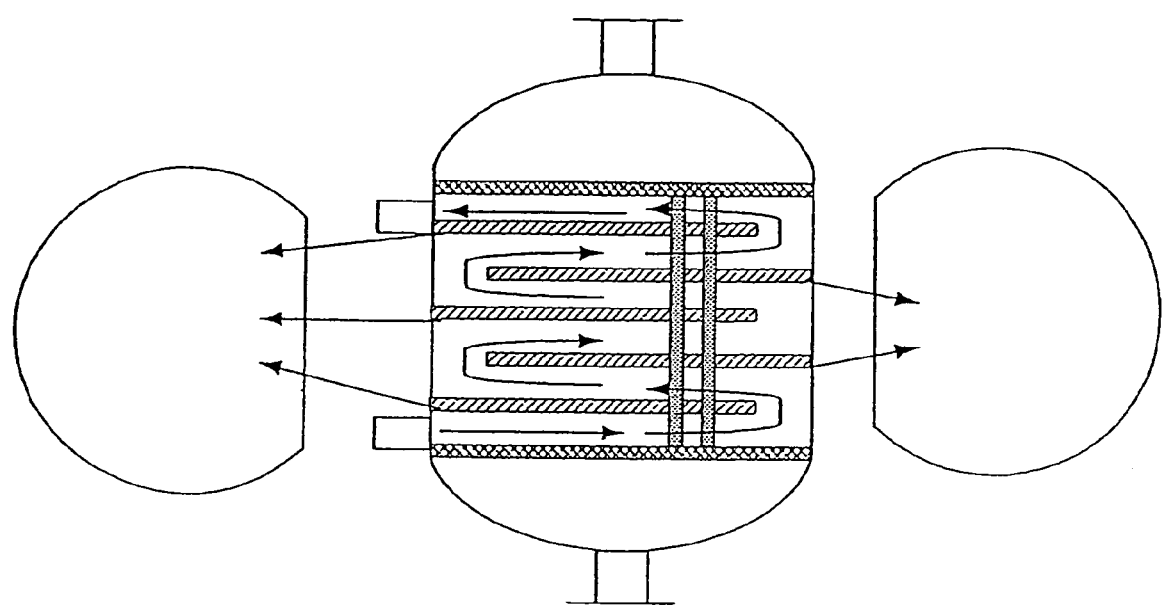
FIG. 4 is a diagram of a mode of a fixed bed multi-tube heat-exchanger type reactor used in the present invention.

A structure of the baffles of the fixed bed multi-tube heat-exchanger type reactor according to the present invention is not particularly limited. Any type of the fixed bed multi-tube heat-exchanger type reactor can be used including a double segment baffle type as shown in FIG. 2, a ring and doughnut baffle type as shown in FIG. 3, and a multi baffle type as shown in FIG. 4, for example. In FIGS. 2 to 4, shapes of the baffles and flow of the heating medium are described.

REFERENCE EXAMPLE 1

The following experiment indicates that the reaction tube located in a portion of poor heat removal can be brought under the same reaction conditions as other reaction tubes by changing the packing specifications of the catalyst.

The fixed bed multi-tube heat-exchanger type reactor consisting of a stainless steel reaction tube having an inner diameter of 27 mm and a length of 5 m was used. Partially hydrogenated triphenyl, which is an organic heating medium, was used as a heating medium. The fixed bed multi-tube heat-exchanger type reactor is of a type capable of circulating the heating medium by an external pump and controlling the volume of the heating medium circulating.

The reaction tube was packed with a mixture containing 80% of an Mo—V—Sb catalyst prepared following a conventional procedure and 20% of alumina balls in volume ratio to a height of 1.8 m and a mixture containing 50% of the catalyst and 50% of the alumina balls in volume ratio to a height of 1.0 m thereon.

A mixed gas consisting of 6 mol % of acrolein, 7 mol % of oxygen, 16 mol % of steam, nitrogen, or the like were fed to the fixed bed multi-tube heat-exchanger type reactor under a condition of a contact time of 2 seconds at a heating medium temperature of 265° C. with the heating medium circulating at 2.5 m$^3$/h.

An acrolein conversion, an acrylic acid yield, and a peak temperature of the catalyst layer at this time were respectively 99%, 97%, and 295° C.

Here, the acrolein conversion and the acrylic acid yield were respectively determined as follows.

Acrolein conversion (mol %)={(moles of acrolein reacted)/(moles of acrolein fed)}×100

Acrylic acid yield (mol %)={(moles of acrylic acid produced)/(moles of acrolein fed)}×100

Further, the peak temperature of the catalyst layer was determined by inserting a multi-point thermocouple (20 points) to the reaction tube and measuring the temperatures of the respective points of measurement.

Next, an experiment was conducted following the same method as described except that the volume of the heating medium circulating was changed to 0.5 m$^3$/h. As a result, the acrolein conversion, the acrylic acid yield, and the peak temperature of the catalyst layer were respectively 99.7%, 95.5%, and 313° C.

Next, an experiment was conducted following the same method as described above with the volume of the heating medium circulating remained at 0.5 m$^3$/h except that the packing specifications of the catalyst in the reaction tube was changed. Here, the Mo—V—Sb catalyst was packed to a height of 1.3 m, and a mixture containing 40% of the catalyst and 60% of the alumina balls in volume ratio was packed thereon to a height of 1.5 m. As a result, the acrolein conversion, the acrylic acid yield, and the peak temperature of the catalyst layer were respectively 99.1%, 97%, and 296° C. The results were similar to the results of the initial experiment circulating the heating medium at 2.5 m$^3$/h.

The above results confirmed that a conversion, an yield, and a peak temperature similar to those obtained in good circulating states of the heating medium (volume of the heating medium circulated at 2.5 m$^3$/h) can be attained by changing the catalyst packing specifications in cases of poor circulating states of the heating medium (volume of the heating medium circulated at 0.5 m$^3$/h as described above).

EXAMPLE 6

Figure 5:
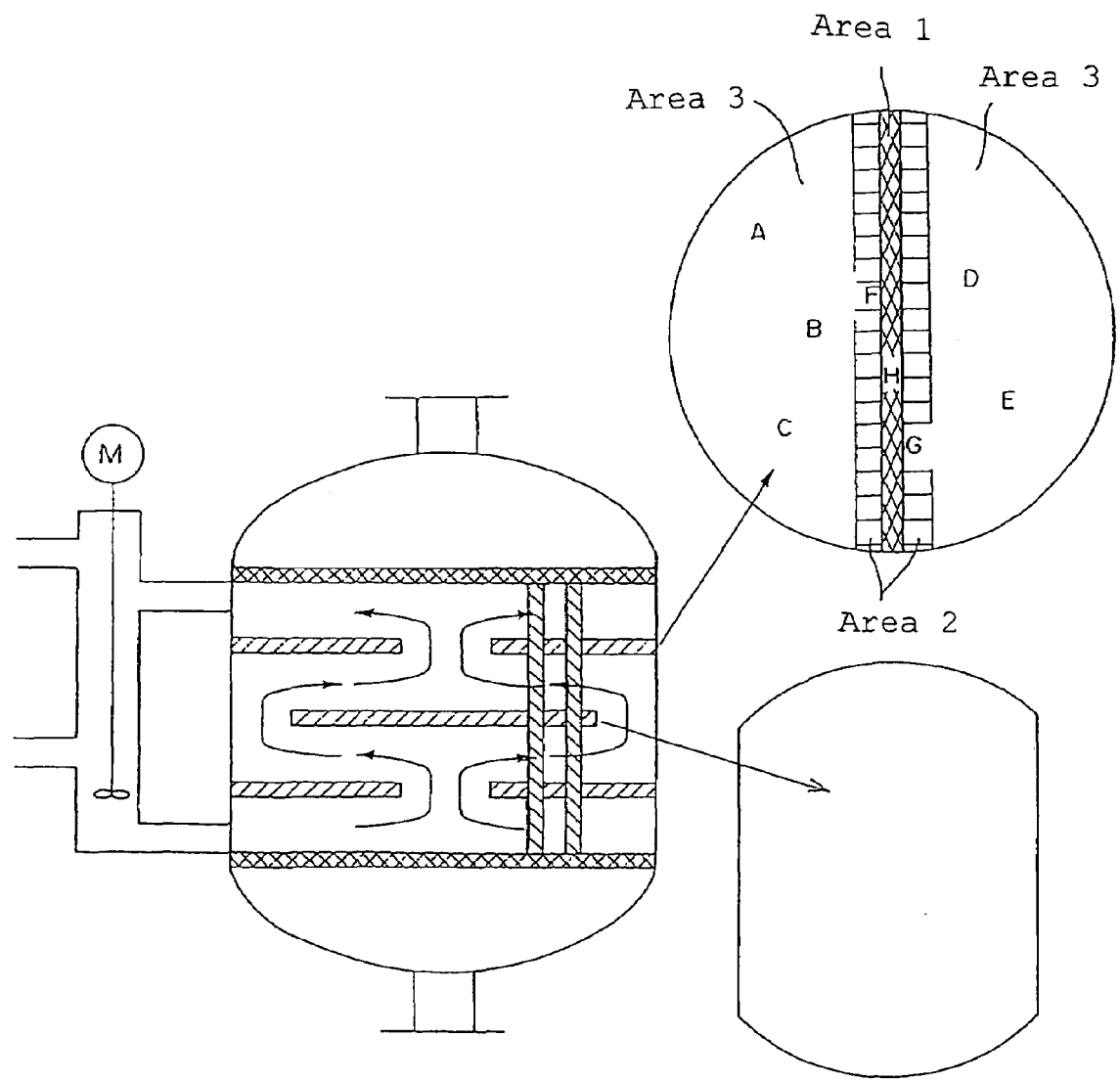
FIG. 5 is a diagram for explaining Example 6 of the present invention.

The multi-point thermocouples were provided for measuring the catalyst layer temperatures of the reaction tubes at positions (A to H) shown in FIG. 5 using the fixed bed multi-tube heat-exchanger type reactor consisting of 20,000 stainless steel reaction tubes having an inner diameter of 27 mm and a length of 3 m. The reactor shell was provided with double segment type baffles for changing a flow path of the heating medium. The partially hydrogenated triphenyl was used as the heating medium.

All of the reaction tubes were packed with a mixture containing 80% of the Mo—V—Sb catalyst, which is the same catalyst as in Example 1, and 20% of alumina balls in volume ratio to a height of 1.8 m and a mixture containing 50% of the catalyst and 50% of the alumina balls in volume ratio to a height of 1.0 m thereon. The alumina balls were further packed thereon to upper portions of the reaction tubes.

A mixed gas consisting of 6 mol % of acrolein, 7 mol % of oxygen, 16 mol % of steam, and the remaining composed of mostly nitrogen and minute acrylic acid, acetic acid, carbon dioxide, carbon monoxide, or the like was fed to the fixed bed multi-tube heat-exchanger type reactor under a condition of a contact time of 2.5 seconds. The temperature of the heating medium at this time was 260° C.

Table 3 shows the peak temperatures of the catalyst layer inside the respective reaction tubes positioned at A to H.

TABLE 3

| Reaction tube position | Catalyst layer peak temperature (° C.) | Difference with the average peak temperature (° C.) |
|---|---|---|
| A | 290 | — |
| B | 291 | — |
| C | 290 | — |

TABLE 3-continued

| Reaction tube position | Catalyst layer peak temperature (° C.) | Difference with the average peak temperature (° C.) |
|---|---|---|
| D | 291 | — |
| E | 291 | — |
| F | 308 | 17 |
| G | 310 | 19 |
| H | 315 | 24 |

The average peak temperature is 291° C., an average value of A to E.

From the results of Table 3, the average peak temperature in this case was defined as 291° C.

The acrolein conversion and the acrylic acid yield at this time were respectively 99.2% and 95.3%.

Next, the catalyst layer peak temperatures of the respective reaction tubes inside the reactor and the average peak temperature were compared. The reaction tubes having a temperature difference of more than 10° C. (the reaction tubes positioned at F, G, and H) were plugged or the packing specifications of the catalyst were changed therefor.

Area 1 described in FIG. 5 was a portion of the poorest heat removal. Therefore, tops and bottoms of the reaction tubes positioned in Area A including H were plugged so that a reactant gas did not flow.

The packing specifications of the reaction tubes positioned in Area 2 including F and G described in FIG. 5 were changed as follows. A mixture containing 90% of the catalyst and 10% of the alumina balls in volume ratio was packed to a height of 1.3 m, and a mixture containing 40% of the catalyst and 60% of the alumina balls in volume ratio was packed thereon to a height of 1.0 m. The alumina balls were further packed thereon to the upper portions of the reaction tubes.

The reaction tubes positioned in Area 3 including A, B, C, D, and E described in FIG. 5 had the catalyst layer peak temperatures comparable to the average peak temperature. Thus, the packing specifications were not changed.

The raw material gas was fed to the reaction tubes of the above specifications under the similar conditions as described above. That is, a mixed gas consisting of 6 mol % of acrolein, 7 mol % of oxygen, 16 mol % of steam, the remaining composed of mostly nitrogen and minute acrylic acid, acetic acid, carbon dioxide, carbon monoxide, or the like was fed to the fixed bed multi-tube heat-exchanger type reactor under a condition of a contact time of 2.5 seconds. The temperature of the heating medium at this time was 262° C.

Table 4 shows the peak temperatures of the catalyst layer inside the respective reaction tubes positioned at A to H.

TABLE 4

| Reaction tube position | Catalyst layer peak temperature (° C.) | Difference with the average peak temperature (° C.) |
|---|---|---|
| A | 291 | — |
| B | 292 | — |
| C | 290 | — |
| D | 291 | — |
| E | 292 | — |
| F | 293 | 2 |
| G | 292 | 1 |
| H | — | — |

The average peak temperature is 291° C., an average value of A to E.

From the results of Table 4, the average peak temperature in this case was defined as 291° C. The results confirmed that the respective reaction tubes had the catalyst layer peak temperatures comparable to the average peak temperature.

The acrolein conversion and the acrylic acid yield at this time were respectively 99.1% and 96.8%.

As described above, the packing specifications of the catalyst layers in the reaction tubes were changed to be in similar reaction states in the same reactor. As a result, nonuniformity of the reaction states was reduced among the respective reaction tubes, and the reaction states of the respective reaction tubes inside the reactor could be made uniform.

From the above, a method for vapor phase catalytic oxidation exhibiting satisfactory results such as effectively preventing formation of hot spots, having high yield of the reaction product gas, and having a long catalyst life could be provided.

<Third Invention>

The catalyst for packing used in the following Examples 7 to 9 was an Mo—Bi catalysts molded into cylinders having an outer diameter of 6 mm, an inner diameter of 2 mm, and a height of 6 mm through tablet compression. Spherical mullite balls having an outer diameter of 6 mm were used as an inert substance for dilution (diluent).

According to the third invention, powdering and degradation are defined as follow:
1) powder ratio: a ratio of powder passed through a screen of 10 mesh with respect to the total normal catalyst; and
2) crack ratio: a ratio of cracked catalyst with respect to the total normal catalyst

EXAMPLE 7

Figure 6:
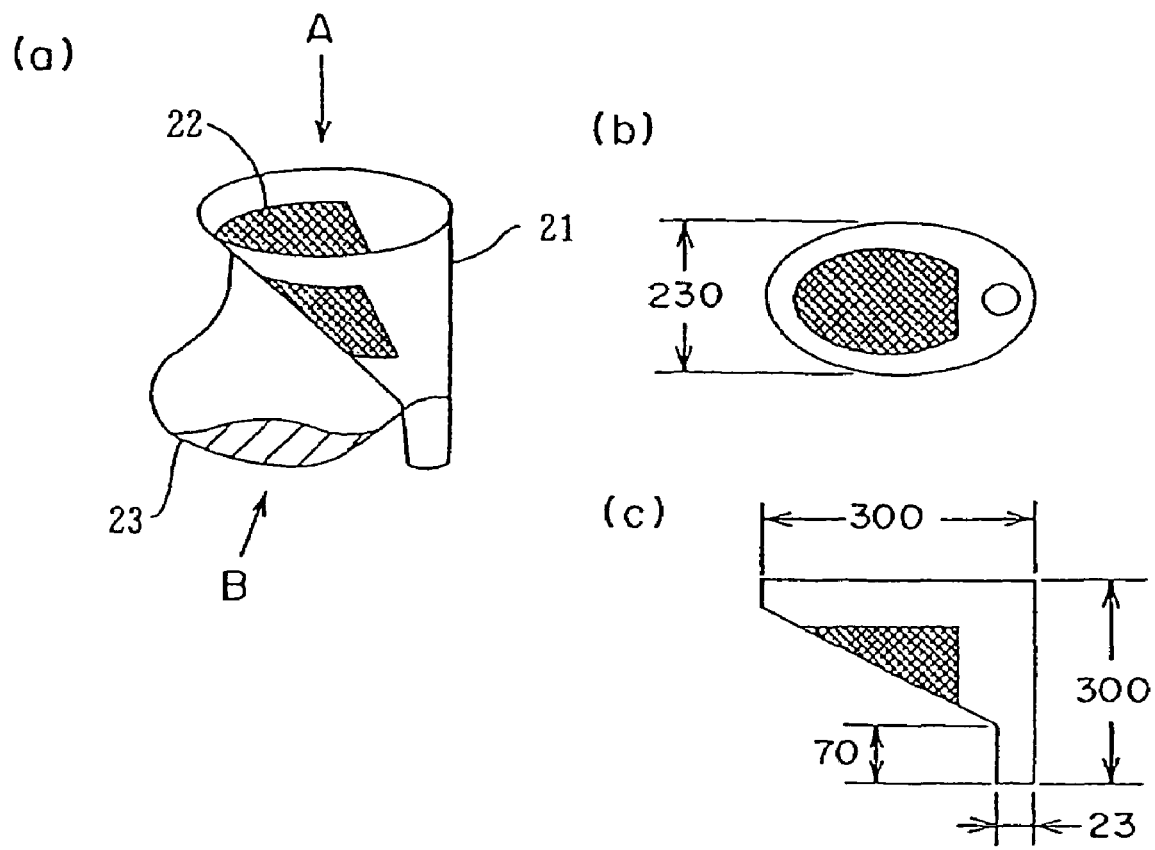
FIG. 6(a) is a perspective view showing an embodiment mode of a funnel used in a catalyst packing method of the present invention.
FIG. 6(b) is a plan view of (a) seen from an A direction.
FIG. 6(c) is a plan view of (a) seen from a B direction.
Figure 7:
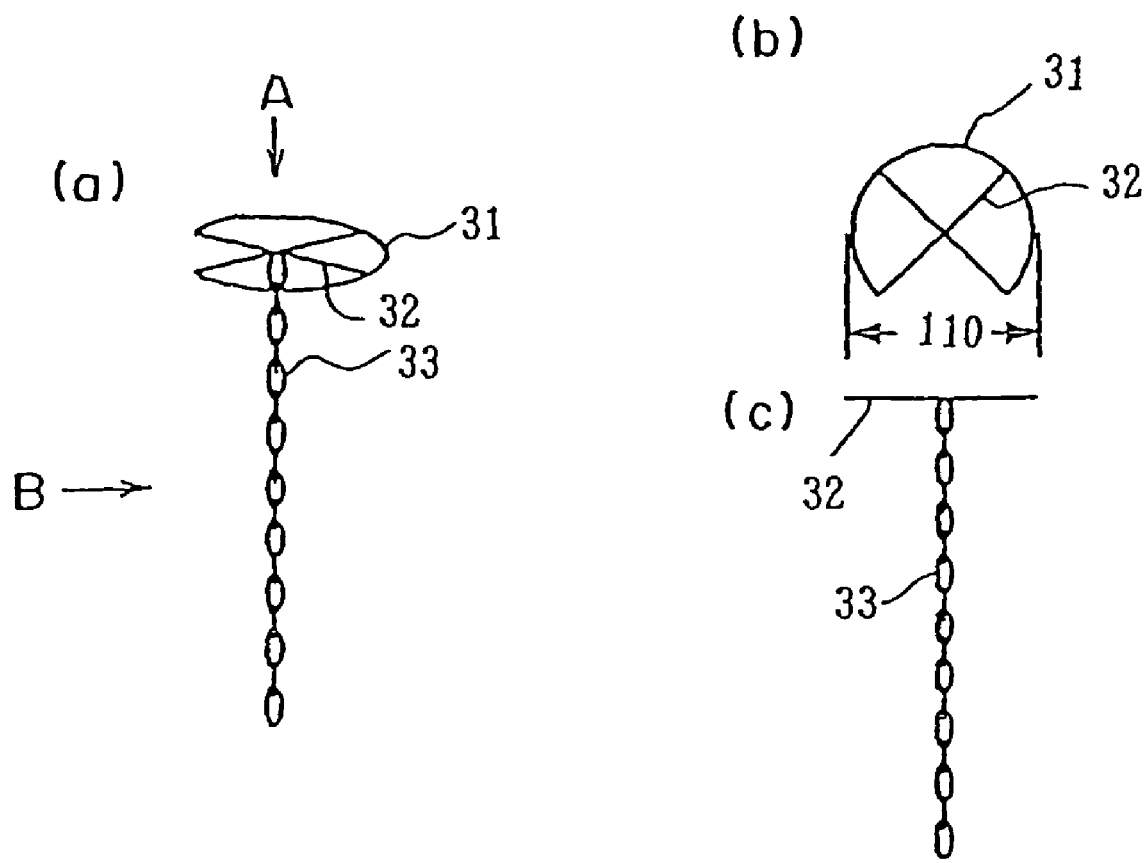
FIG. 7(a) is a perspective view showing an embodiment mode of a chain substance used in a catalyst packing method of the present invention.
FIG. 7(b) is a plan view of (a) seen from an A direction.
FIG. 7(c) is a plan view of (a) seen from a B direction.
Figure 8:
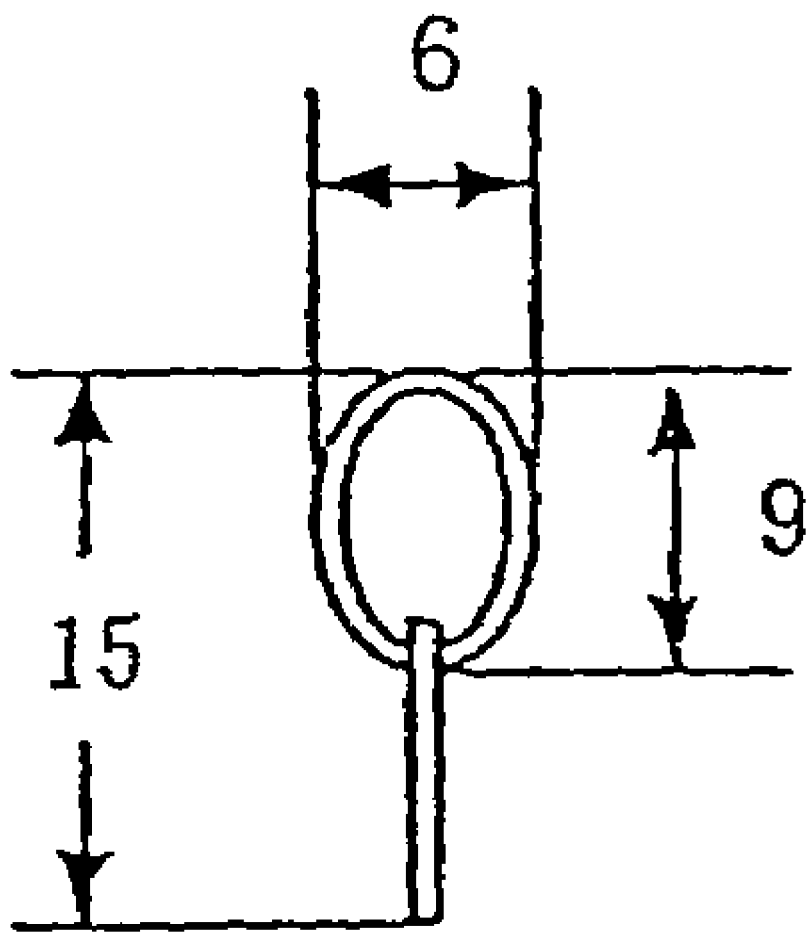
FIG. 8 is an enlarged view showing an embodiment mode of a chain substance used in a catalyst packing method of the present invention.

The catalyst was packed in the reaction tube of the fixed bed multi-tube reactor using a packing funnel with a wire net shown in FIG. 6. The packing funnel had a net mesh of 3 mm and an angle of inclination of the wire net portion of 35°. A polyethylene bucket was set at a lower portion of the packing funnel. 580 g of the Mo—Bi catalyst, as a single catalyst, was allowed to fall from the end of the packing funnel in 60 seconds. The powder ratio and the crack ratio of the catalyst separated below the wire net at this time were respectively 0.51% and 1.04%, and a recovery rate of the powdered or degraded catalyst was substantially 100%.

The recovery rate of the powdered or degraded catalyst was obtained by removing the packed catalyst without powdering or degrading and was represented as a ratio with respect to the total catalyst removed following the definitions of the 1) powder ratio and the 2) crack ratio.

EXAMPLE 8

580 g of the Mo—Bi catalyst, as a single catalyst, was allowed-to fall from the end of the packing funnel in 60 seconds under same conditions as in Example 7 except that the angle of the inclination of the wire net portion of the packing funnel was changed to 50°. The powder ratio and the crack ratio of the catalyst separated below the wire net at this time were respectively 0.6% and 0.84%, and recovery and separation rate of the catalyst at the wire net was about 90%.

EXAMPLE 9

The catalyst was packed in the reaction tube of the fixed bed multi-tube reactor using a packing funnel with a wire net shown in FIG. 6. The packing funnel had a wire net mesh of 4 mm and an angle of inclination of the wire net portion of 45°. A polyethylene bucket was set at a lower portion of the packing funnel. 175 g of the Mo—Bi catalyst and 220g of a diluent were allowed to fall from the end of the packing funnel in 40 seconds. The powder ratio and the crack ratio of the catalyst separated below the wire net at this time were respectively 0.51% and 1.29%, and recovery rate of the powdered or degraded catalyst was 95%.

<Fourth Invention>

Hereinafter, the catalysts for packing used in Examples 10 to 13 were prepared as follows.

94.1 g of ammonium paramolybdate was dissolved in 400 ml of pure water by heating. Next, 7.18 g of ferric nitrate, 25.8 g of cobalt nitrate, and 38.7 g of nickel nitrate were dissolved in 60 ml of pure water by warming. The two liquid mixtures were gradually mixed with sufficient stirring.

Next, to the mixed liquid (slurry), a liquid mixture containing 0.85 g of borax, 0.38 g of sodium nitrate, and 0.36 g of potassium nitrate dissolved in 40 ml of pure water by warming was added and sufficiently stirred. Then, 57.8 g of bismuth subcarbonate and 64 g of silica were added to the slurry for mixing under stirring. The slurry was subjected to drying by heating, and then to heat treatment in air at 300° C. for 1 hour. The obtained solid was molded into cylinders having an outer diameter of 6 mm, an inner diameter of 2 mm, and a height of 6 mm through table compression using a compact molding device. The cylinders were calcined in a muffle furnace at 480° C. for 8 hours, to thereby obtain a catalyst. The obtained catalyst is a mixed oxide having the following atomic ratio, which is a composition ratio of metal components of the catalyst calculated from the raw materials.

Mo:Bi:Co:Ni:Fe:Na:B:K:Si=12:5:2:3:0.4:0.2:0.2: 0.08:24

The obtained catalyst was an Mo—Bi catalyst molded into cylinders having an outer diameter of 6 mm, an inner diameter of 2 mm, and a height of 6 mm through tablet compression. Spherical mullite balls having an outer diameter of 6 mm were used as an inert substance for dilution (diluent).

According to the fourth invention, powdering and degradation are defined as follows:
1) powder ratio: a ratio of powder passed through a screen of 14 mesh with respect to the total normal catalyst; and
2) crack ratio: a ratio of cracked catalyst with respect to the total normal catalyst.

EXAMPLE 10

A stainless steel spring was fixed at a bottom portion of a stainless steel straight pipe having an inner diameter of 26.6 mm and a pipe length of 4.4 m at a position 50 mm above the bottom portion of the straight pipe. A stainless steel chain having a length of 2.65 m and consisting of an oval ring member having a wire diameter of 1.5 mm and an outer diameter of 6 mm×9 mm was hanged (free fall distance of 1.7 m) from an upper portion of a reaction tube. 650 g of the Mo—Bi catalyst as a single catalyst was packed by allowing the catalyst to fall from the upper portion. Note that a distance between a lower end of the chain and an upper end of the catalyst layer was 5 cm. The powder ratio and the crack ratio at this time were respectively 0.2% and 3.1%.

COMPARATIVE EXAMPLE 5

650 g of the Mo—Bi catalyst as a single catalyst was packed by allowing the catalyst to fall as in Example 10 except that a chain was not used (free fall distance of 4.35 m). The powder ratio and the crack ratio at this time were respectively 0.9% and 25.0%.

EXAMPLE 11

A stainless steel spring was fixed in the reaction tube of the Example 10 at a position 1.55 m above the bottom portion of the reaction tube. A chain having a length of 1.85 m was hanged (free fall distance of 1.0 m) from the upper portion of the reaction tube. A diluent catalyst containing 195 g of the Mo—Bi catalyst and 240 g of the diluent mixed was packed by allowing the catalyst to fall from the upper portion. Note that a distance between the lower end of the chain and the upper end of the catalyst layer was 5 cm. The powder ratio and the crack ratio at this time were respectively 0.4% and 4.8%.

COMPARATIVE EXAMPLE 6

The diluent catalyst in Example 11 was packed by allowing the catalyst to fall as in Example 11 except that a chain was not inserted (free fall distance of 2.85 m). The powder ratio and the crack ratio at this time were respectively 0.9% and 19.4%.

EXAMPLE 12

A stainless steel spring was fixed in the reaction tube of the Example 10 at a position 2.55 m above the bottom portion of the reaction tube. A chain having a length of 0.9 m was hanged (free fall distance of 0.95 m) from the upper portion of the reaction tube. A diluent catalyst containing 140 g of the Mo—Bi catalyst and 345 g of the diluent mixed was packed by allowing the catalyst to fall from the upper portion. Note that a distance between the lower end of the chain and the upper end of the catalyst layer was 50 cm. The powder ratio and the crack ratio at this time were respectively 0.3% and 5.6%.

COMPARATIVE EXAMPLE 7

The diluent catalyst in Example 12 was packed by allowing the catalyst to fall as in Example 12 except that a chain was not inserted (free fall distance of 1.85 m). The powder ratio and the crack ratio at this time were respectively 0.6% and 13.4%.

EXAMPLE 13

A stainless steel spring was fixed at a bottom portion of a polycarbonate straight pipe having an inner diameter of 24.0 mm and a pipe length of 1.0 m. A chain having a length of 0.7 m was hanged (free fall distance of 0.3 m) from the upper portion of the reaction tube. 35 g of the Mo—Bi catalyst as a single catalyst was packed by allowing the catalyst to fall. Note that a distance between the lower end of the chain and the upper end of the catalyst layer was 2 cm. The powder ratio and the crack ratio at this time were respectively 0.3% and 0.9%.

COMPARATIVE EXAMPLE 8

35 g of the Mo—Bi catalyst as a single catalyst was packed by allowing the catalyst to fall as in Example 13 except that a chain was not inserted (free fall distance of 1.0 m) The powder ratio and the crack ratio at this time were respectively 0.3% and 3.0%.

INDUSTRIAL APPLICABILITY

According to the first invention of the present invention, in a method for producing acrolein and acrylic acid, and the like from a raw material gas such as propane and propylene through vapor phase catalytic oxidation with molecular oxygen or a molecular oxygen-containing gas using a fixed bed multi-tube heat-exchanger type reactor, not only are the variations of the reaction states among the respective reaction tubes suppressed and is the improvement on catalyst life achieved, but also acrolein, acrylic acid, and the like can be produced in high yields. Such results can be obtained by packing the catalyst in the respective reaction tubes of the fixed bed multi-tube heat-exchanger type reactor and then using the reactor for reaction after adjusting the pressure loss of the reaction tubes to be uniform.

Further, according to the second invention of the present invention, a method for vapor phase catalytic oxidation achieving satisfactory results such as effectively preventing hot spot formation, yielding a large volume of the reaction product gas, and extending catalyst life can be provided. These satisfactory results may be obtained by using the fixed bed multi-tube heat-exchanger type reactor provided with a plurality of reaction tubes, circulating a heating medium outside the reaction tubes, and feeding the raw material gas inside the reaction tubes packed with the catalyst.

Further, according to the third invention of the present invention, the use of the funnel with a net in at least a part of the funnel for packing the catalyst in the reaction tubes of the fixed bed multi-tube reactor allows substantially complete separation or removal of the powdered or degraded catalyst generated during transfer, transport, and handling of the catalyst. Therefore, mechanical strength of the catalyst does not have to be increased more than necessary concerning powdering or the like of the catalyst during packing thereof. Limitations on catalyst design become small, enabling catalyst preparation under a broad range of conditions.

According to the fourth invention of the present invention, the resistance of the chain substance can remarkably reduce powdering or degradation of the catalyst caused by physical impact during falling of the catalyst, when packing the catalyst in the fixed bed multi-tube reactor. Therefore, mechanical strength of the catalyst does not have to be increased more than necessary concerning powdering or the like of the catalyst during packing thereof. Limitations on catalyst design become small, enabling catalyst preparation under a broad range of conditions. Further, blocking can be prevented during catalyst packing.

The invention claimed is:

1. A method for vapor phase catalytic oxidation for obtaining a reaction product gas by using a fixed bed multi-tube heat-exchanger type reactor provided with a plurality of reaction tubes, circulating a heating medium outside the reaction tubes, and feeding a raw material gas inside the reaction tubes packed with a catalyst, wherein the method comprises:

conducting a fluid analysis of the heating medium through a simulation analysis using a computer;

predicting peak temperatures of catalyst layers of respective reaction tubes; and determining a structure of the catalyst layers of the respective reaction tubes so that a value obtained by subtracting an average value, representing a whole reactor, of peak temperatures of the catalyst layers of the respective reaction tubes from the peak temperatures, is less than 15° C.

2. The method for vapor phase catalytic oxidation according to claim 1, wherein the heating medium is for absorbing heat of reaction generated from the reaction tubes.

3. The method for vapor phase catalytic oxidation according to claim 1, wherein the peak temperatures of the catalyst layers of the respective reaction tubes are predicted by measuring catalyst layer temperatures of the reaction tubes.

4. The method for vapor phase catalytic oxidation according to claim 1, wherein the peak temperatures of the catalyst layers of the respective reaction tubes are predicted through a simulation analysis using a computer.

5. The method for vapor phase catalytic oxidation according to claim 4, wherein the fluid analysis of the heating medium and an analysis of the peak temperatures of the catalyst layers of the respective reaction tubes are conducted through the simulation analysis using a computer.

6. The method for vapor phase catalytic oxidation according to claim 1, wherein items determining the structure of the catalyst layers of the respective reaction tubes include items of a catalyst type, a catalyst amount, a catalyst shape, a dilution method for the catalyst, and lengths of reaction zones.

7. The method for vapor phase catalytic oxidation according to claim 1, wherein the method further comprises:

stopping feed of the raw material gas to the reaction tubes for a part of the reaction tubes among the plurality of reaction tubes in the fixed bed multi-tube heat-exchanger type reactor.

* * * * *